(12) United States Patent
Li

(10) Patent No.: US 12,310,781 B2
(45) Date of Patent: May 27, 2025

(54) COLLIMATORS, IMAGING DEVICES, AND METHODS FOR TRACKING AND CALIBRATING X-RAY FOCUS POSITIONS

(71) Applicant: SHANGHAI UNITED IMAGING HEALTHCARE CO., LTD., Shanghai (CN)

(72) Inventor: Bing Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 402 days.

(21) Appl. No.: 17/821,474

(22) Filed: Aug. 22, 2022

(65) Prior Publication Data
US 2022/0401058 A1 Dec. 22, 2022

Related U.S. Application Data

(62) Division of application No. 16/100,811, filed on Aug. 10, 2018, now Pat. No. 11,419,572.

(30) Foreign Application Priority Data

Sep. 29, 2017 (CN) .......................... 201710927155.3

(51) Int. Cl.
A61B 6/58 (2024.01)
A61B 6/00 (2024.01)
(Continued)

(52) U.S. Cl.
CPC .............. A61B 6/585 (2013.01); A61B 6/032 (2013.01); A61B 6/06 (2013.01); A61B 6/4021 (2013.01);
(Continued)

(58) Field of Classification Search
CPC ......... A61B 6/032; A61B 6/06; A61B 6/4021; A61B 6/405; A61B 6/4291; A61B 6/542;
(Continued)

(56) References Cited

U.S. PATENT DOCUMENTS 5,430,298 A 7/1995 Possin et al.
5,970,118 A 10/1999 Sokolov
(Continued)

FOREIGN PATENT DOCUMENTS

CN 1360224 A 7/2002
CN 101762613 A 6/2010
(Continued)

OTHER PUBLICATIONS

First Office Action in Chinese Application No. 201710927155.3 mailed on Mar. 20, 2020, 19 pages.

Primary Examiner — Dani Fox
Assistant Examiner — Soorena Kefayati
(74) Attorney, Agent, or Firm — METIS IP LLC

(57) ABSTRACT

An imaging device is provided. The imaging device includes an X-ray tube, a collimator, and a detector. The collimator includes an opening, wherein the collimator has a width in a first direction and a length in a second direction. The opening has an opening width in the width direction of the collimator, and an opening at at least one end of the collimator in the second direction has an opening width smaller than that of an opening within the middle section of the collimator.

20 Claims, 16 Drawing Sheets

(51) Int. Cl.
    *A61B 6/03*     (2006.01)
    *A61B 6/06*     (2006.01)
    *A61B 6/40*     (2024.01)
    *A61B 6/42*     (2024.01)
    *G21K 1/02*     (2006.01)

(52) U.S. Cl.
    CPC ............ *A61B 6/4291* (2013.01); *A61B 6/542* (2013.01); *A61B 6/547* (2013.01); *A61B 6/582* (2013.01); *A61B 6/586* (2013.01); *G21K 1/025* (2013.01); *A61B 6/405* (2013.01)

(58) Field of Classification Search
    CPC ......... A61B 6/547; A61B 6/582; A61B 6/585; A61B 6/586; G21K 1/025
    See application file for complete search history.

(56) References Cited

U.S. PATENT DOCUMENTS

| | | | |
|---|---|---|---|
| 6,438,210 | B1 | 8/2002 | Castleberry |
| 9,966,158 | B2 | 5/2018 | Reitz et al. |
| 10,779,778 | B2 | 9/2020 | Rui et al. |
| 10,994,155 | B1 | 5/2021 | Renner |
| 2002/0015474 | A1 | 2/2002 | Tybinkowski et al. |
| 2005/0105691 | A1 | 5/2005 | Ikhlef |
| 2005/0129175 | A1* | 6/2005 | Shen ............... A61B 6/583 378/62 |
| 2006/0233298 | A1 | 10/2006 | Igarashi et al. |
| 2007/0071161 | A1 | 3/2007 | Sakuta |
| 2009/0225954 | A1 | 9/2009 | McKim et al. |
| 2010/0096777 | A1 | 4/2010 | Appleby et al. |
| 2010/0189376 | A1* | 7/2010 | Bertram ............. G06T 5/73 382/274 |
| 2010/0202591 | A1 | 8/2010 | McKim et al. |
| 2010/0303202 | A1* | 12/2010 | Ren ............... A61B 6/502 378/62 |
| 2011/0014474 | A1 | 1/2011 | Appleby et al. |
| 2011/0164727 | A1 | 7/2011 | Tonami |
| 2011/0176663 | A1* | 7/2011 | Shaughnessy ......... A61B 6/032 378/207 |
| 2011/0293069 | A1 | 12/2011 | Roberts |
| 2012/0140874 | A1 | 6/2012 | Li et al. |
| 2012/0148016 | A1 | 6/2012 | Blevis |
| 2012/0177272 | A1 | 7/2012 | Suzuki et al. |
| 2012/0201349 | A1 | 8/2012 | Kaneko et al. |
| 2013/0026380 | A1 | 1/2013 | Tkaczyk et al. |
| 2013/0161520 | A1 | 6/2013 | Jansen |
| 2013/0223588 | A1* | 8/2013 | Kurochi ............. A61B 6/06 378/19 |
| 2013/0308748 | A1* | 11/2013 | Ikhlef ............. A61B 6/4078 250/336.1 |
| 2013/0336448 | A1 | 12/2013 | Demianovich |
| 2014/0034838 | A1 | 2/2014 | Appleby et al. |
| 2014/0138556 | A1 | 5/2014 | Shahar et al. |
| 2014/0146948 | A1 | 5/2014 | Zhang et al. |
| 2014/0177781 | A1 | 6/2014 | Singh et al. |
| 2014/0355734 | A1 | 12/2014 | Ying |
| 2015/0049857 | A1* | 2/2015 | Wiedmann ........... A61B 6/032 378/19 |
| 2015/0216498 | A1* | 8/2015 | Schulze ............. A61B 6/584 378/207 |
| 2015/0321025 | A1 | 11/2015 | Freud et al. |
| 2016/0199019 | A1* | 7/2016 | Ruimi ............ A61B 6/5258 378/16 |
| 2017/0209106 | A1* | 7/2017 | Ikhlef ............ A61B 6/06 |
| 2017/0269234 | A1* | 9/2017 | Sjolin ............ A61B 6/588 |
| 2018/0047156 | A1* | 2/2018 | Rudin ............ G06T 3/40 |
| 2018/0168522 | A1 | 6/2018 | Budde et al. |
| 2018/0177481 | A1* | 6/2018 | Jacob ............ G01T 1/242 |
| 2018/0279457 | A1* | 9/2018 | Miller ............ A61B 6/032 |
| 2018/0368790 | A1 | 12/2018 | Ishitsu et al. |
| 2019/0008474 | A1* | 1/2019 | Sjolin ............ G01T 1/24 |
| 2019/0378631 | A1 | 12/2019 | Thran et al. |

FOREIGN PATENT DOCUMENTS

| | | |
|---|---|---|
| CN | 104783822 A | 7/2015 |
| JP | 2014018592 A | 2/2014 |

* cited by examiner

COLLIMATORS, IMAGING DEVICES, AND METHODS FOR TRACKING AND CALIBRATING X-RAY FOCUS POSITIONS

CROSS-REFERENCE TO RELATED APPLICATIONS

This application is a divisional application of U.S. patent application Ser. No. 16/100,811, filed on Aug. 10, 2018, which claims priority of Chinese Application No. 201710927155.3 filed on Sep. 29, 2017, the entire contents of which are hereby incorporated by reference.

TECHNICAL FIELD

The application generally relates to imaging, and more specifically, relates to a system and method for tracking and/or correcting the focus position of a radiation source in an imaging device.

BACKGROUND

During a computed tomography (CT) scanning, focus positions of X-ray beams emitted from an X-ray tube may change due to effects from external environments and other factors. For example, a rotation shaft of the X-ray tube may thermally expand due to heat accumulation, which may lead to a focus position offset, and have an impact on the scanning. Moreover, due to effects of environmental changes, in CT imaging, it is needed to perform an air correction. The focus position of the X-ray tube of the CT scanner during the air correction may be different from the focus position of the X-ray tube of the CT scanner during the scanning of a patient, which may cause artifacts in a reconstructed image. Therefore, there is a need for a method for tracking the position of the focus of the X-ray tube of a CT scanner to identify, reduce, or eliminate the impact of a focus position offset on imaging.

SUMMARY

In a first aspect of the present disclosure, an imaging device is provided. The imaging device may include an X-ray tube, a detector, and a collimator. The collimator may include an opening. The opening may have a plurality of opening widths along a first direction and a plurality of opening lengths along a second direction. The plurality of opening widths may include a first opening width and a second opening width. The first opening width may correspond to at least one end of the opening. The second opening width may correspond to a middle section of the opening, and the first opening width may be smaller than the second opening width.

In some embodiments, the collimator may include a protrusion at at least one end in the second direction, and the protrusion may protrude into the opening.

In some embodiments, the collimator may be an anti-scatter grid. The anti-scatter grid may include a plurality of sub-openings, and the plurality of sub-openings may be configured corresponding to a plurality of detection units of a detector.

In some embodiments, the anti-scatter grid may include a body and a plurality of protrusions. The plurality of protrusions may be located at an edge of the body extending along the first direction. The plurality of protrusions may be arranged along the edge of the body, and each of the plurality of protrusions may partially block a corresponding detection unit.

In a second aspect of the present disclosure, a method for determining a focus position offset of an X-ray tube of an imaging device is provided. The method may be implemented on at least one device each of which has at least one processor and storage. The method may include one or more of the following operations. A first ray intensity distribution detected by an edge detection unit of a detector of the imaging device may be obtained. The imaging device may include an X-ray tube, a detector, and a collimator. The collimator may include an opening and a protrusion. The protrusion may be configured at at least one end of the opening and protruding into the opening. The opening may have a plurality of opening widths along a first direction and a plurality of opening lengths along a second direction. A first opening width corresponding to at least one end of the collimator in the second direction may be smaller than a second opening width corresponding to a middle section of the collimator in the second direction. The edge detection unit may be located at an edge of the detector along the first direction. A size of the edge detection unit along the second direction may correspond to a size of the protrusion along the second direction. The first ray intensity distribution may correspond to a first focus position of the X-ray tube. A second ray intensity distribution detected by the edge detection unit may be obtained. The second ray intensity distribution may correspond to a second focus position of the X-ray tube. The focus position offset that is between the first focus position and the second focus position of the X-ray tube may be determined based on the first ray intensity distribution and the second ray intensity distribution.

In some embodiments, the method may include one or more of the following operations. A first detection unit that corresponds to a boundary of the first ray intensity distribution may be determined. A second detection unit that corresponds to a boundary of the second ray intensity distribution may be determined. The focus position offset may be determined based on a distance between the first detection unit and the second detection unit.

In a third aspect of the present disclosure, a method for tracking a focus position of an X-ray tube of an imaging device is provided. The method may be implemented on at least one device each of which has at least one processor and storage. The method may include one or more of the following operations. A ray intensity distribution detected by an edge detection unit of a detector of the imaging device may be obtained. The imaging device may include an X-ray tube, a detector, and a collimator. The collimator may include an opening and a protrusion. The protrusion may be configured at at least one end of the opening and protruding into the opening. The opening may have a plurality of opening widths along a first direction and a plurality of opening lengths along a second direction. The plurality of opening widths may include a first opening width and a second opening width. The first opening width may correspond to at least one end of the collimator in the second direction. The second opening width may correspond to a middle section of the collimator in the second direction, and the first opening width may be smaller than the second opening width. The edge detection unit may be located at an edge of the detector along the first direction. A size of the edge detection unit along the second direction may correspond to a size of the protrusion along the second direction. Each ray intensity of the ray intensity distribution may correspond to a focus position of the X-ray tube. A first boundary intensity and a second boundary intensity of the ray intensity distribution may be determined. A relationship between the first boundary intensity and the second boundary intensity may be determined. The focus position of the X-ray tube may be determined by consulting a mapping table based on the relationship between the first boundary intensity and the second boundary intensity. The mapping table may include a correspondence relationship between focus positions and the relationship between the first boundary intensity and the second boundary intensity.

In a fourth aspect of the present disclosure, a system for tracking a focus position of an X-ray tube of an imaging device is provided. The system may include a storage device configured to store a computer program and a processor configured to communicate with the storage device. When executing the set of instructions, the processor may be configured to cause the system to: obtain a ray intensity distribution detected by an edge detection unit of a detector of the imaging device, wherein the imaging device includes an X-ray tube, a detector and a collimator, the collimator includes: an opening and a protrusion, the protrusion being configured at at least one end of the opening and protruding into the opening, the opening having a plurality of opening widths along a first direction and a plurality of opening lengths along a second direction, the plurality of opening widths including a first opening width and a second opening width, the first opening width corresponding to at least one end of the collimator in the second direction, the second opening width corresponding to a middle section of the collimator in the second direction, and the first opening width being smaller than the second opening width, wherein the edge detection unit may be located at the edge of the detector along the first direction, a size of the edge detection unit along the second direction may correspond to a size of the protrusion along the second direction, and each ray intensity of the ray intensity distribution may correspond to a focus position of the X-ray tube; determine a first boundary intensity and a second boundary intensity of the ray intensity distribution; determine a relationship between the first boundary intensity and the second boundary intensity; and determine, by consulting a mapping table, the focus position of the X-ray tube based on the relationship between the first boundary intensity and the second boundary intensity, wherein the mapping table includes a correspondence relationship between focus positions and the relationship between the first boundary intensity and the second boundary intensity.

In a fifth aspect of the present disclosure, a calibration system for tracking a focus position of an X-ray tube of an imaging device is provided. The system may include a storage device configured to store a computer program and a processor configured to communicate with the storage device. When executing the set of instructions, the processor may be configured to cause the system to: obtain a first detector response corresponding to a first focus position by scanning a reference object; obtain a second detector response corresponding to a second focus position by scanning a target object; determine, by consulting a correction table, a third detector response corresponding to the first focus position and a fourth detector response corresponding to the second focus position, wherein the correction table includes a correspondence relationship between focus positions and detector responses; calibrate the first detector response based on the third detector response and the fourth detector response; obtain image data corresponding to the target object based on the calibrated first detector response and the second detector response; and generate an image based on the image data.

In a sixth aspect of the present disclosure, a method for calibrating a focus position of an imaging device is provided. The method may be implemented on at least one device, each of which has at least one processor and storage. The method may include one or more of the following operations. A first detector response corresponding to a first focus position may be obtained by scanning a reference object. A second detector response corresponding to a second focus position may be obtained by scanning a target object. A third detector response corresponding to the first focus position and a fourth detector response corresponding to the second focus position may be determined by consulting a correction table. The correction table may include a correspondence relationship between focus positions and detector responses. The first detector response may be calibrated based on the third detector response and the fourth detector response. Image data corresponding to the target object may be obtained based on the calibrated first detector response and the second detector response. An image may be generated based on the image data.

In some embodiments, the method may include one or more of the following operations. A calibration value may be determined based on the third detector response and the fourth detector response. The first detector response may be calibrated based on the calibration value.

In some embodiments, the method may include one or more of the following operations. The first focus position and/or the second focus position may be determined based on a ray intensity distribution detected by an edge detection unit of a detector of an imaging device. The imaging device may include an X-ray tube, a detector, and a collimator. The collimator may include an opening and a protrusion. The protrusion may be configured at at least one end of the opening and protruding into the opening. The opening may have a plurality of opening widths along a first direction and a plurality of opening lengths along a second direction. The plurality of opening widths may include a first opening width and a second opening width. The first opening width may correspond to at least one end of the collimator in the second direction. The second opening width may correspond to a middle section of the collimator in the second direction, and the first opening width may be smaller than the second opening width. The edge detection unit may be located at an edge of the detector along the first direction. A size of the edge detection unit along the second direction may correspond to a size of a protrusion along the second direction. Each ray intensity of the ray intensity distribution may correspond to a focus position of an X-ray tube.

In a seventh aspect of the present disclosure, a collimator is provided. The collimator may include an opening. The opening may have a plurality of opening widths along a first direction and a plurality of opening lengths along a second direction. The plurality of opening widths may include a first opening width and a second opening width. The first opening width may correspond to at least one end of the collimator in the second direction. The second opening width may correspond to a middle section of the collimator in the second direction, and the first opening width may be smaller than the second opening width.

In some embodiments, the collimator may include a blade.

In some embodiments, the blade may include a protrusion at at least one end in the second direction, and the protrusion may protrude into the opening.

In some embodiments, the collimator may be an anti-scatter grid.

In some embodiments, the anti-scatter grid may include a plurality of sub-openings, and the plurality of sub-openings may be configured corresponding to a plurality of detection units of a detector.

In some embodiments, the anti-scatter grid may include a body and a plurality of protrusions. The plurality of protrusions may be located at an edge of the body and protruding along the first direction. Each of the plurality of protrusions may partially block a corresponding detection unit.

In some embodiments, the opening may be a substantially rectangular opening, and at least one corner of the opening may include a protrusion protruding into the opening.

In some embodiments, the collimator may include a pair of blocks disposed opposite to each other. The pair of blocks may define an opening, and at least one end of a block of the pair of blocks may include a protrusion protruding into the opening.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

Figure 1:
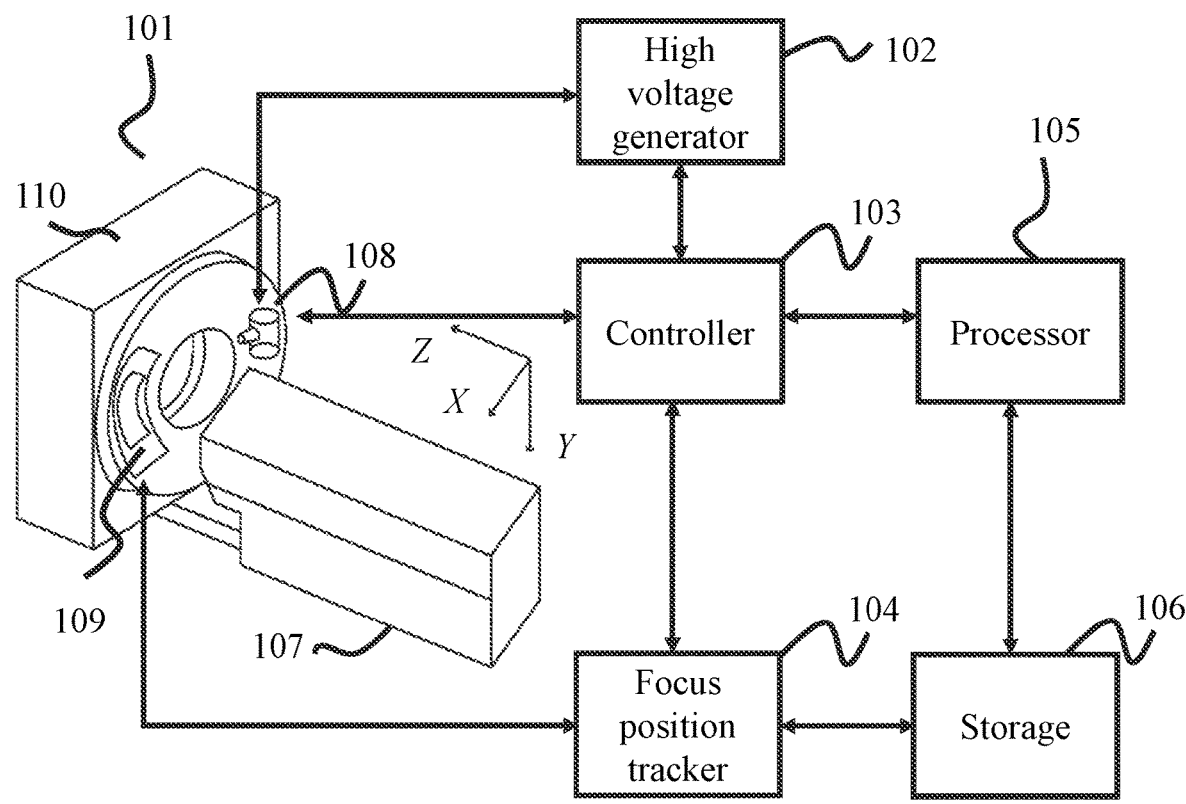
FIG. 1 is a schematic diagram illustrating an exemplary imaging system according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., data processing device 105 as illustrated in FIG. 1) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included of connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The following description is provided to help better understand methods or systems in the present disclosure. The imaging system described below may be applied in imaging, such as disease diagnosis and research, as well as industry. The imaging system may be a single-modality system, or a multi-modality system, including but not limited to a computed tomography (CT) system, a positron emission tomography (PET) system, a magnetic resonance imaging (MRI) system, an ultrasound scan (US) system, a single-photon emission computed tomography (SPECT) system, PET-CT, US-CT, PET-MRI or the like, or a combination thereof. The system and method disclosed herein may track and/or correct the focus position of a radiation source in an imaging device. The focus position of the radiation source (or referred to as a radiation generator) may shift due to, e.g., heat generated by the imaging device or a portion thereof, e.g., by the radiation source. Merely by way of example, the imaging device is a CT scanner, and the radiation generator of the CT scanner includes an X-ray tube.

FIG. 1 is a schematic diagram illustrating an exemplary imaging system according to some embodiments of the present disclosure. The imaging system 100 may scan a target object, and generate an image related to the target object based on scanning signals. In some embodiments, the imaging system 100 may be a medical imaging system. The imaging system 100 may include a data acquisition device 101, a high voltage generator 102, a controller 103, a focus position tracker 104, a data processing device 105, and storage 106.

The data acquisition device 101 may scan a target object, and obtain corresponding scanning signals. The data acquisition device 101 may be a computed tomography (CT) scanner, a positron emission tomography (PET) scanner, a magnetic resonance imaging (MRI) scanner, a medical electronic endoscope (MEE), or the like, or any combination thereof. In some embodiments, the data acquisition device 101 may be a CT device.

Merely for illustration purposes, the data acquisition device 101 may be a CT device. The data acquisition device 101 may include a table 107, a radiation generator 108, a detector 109, and a gantry 110. The table 107 may support a target object (e.g., a patient to be diagnosed). During a CT scanning, the table 107 may move the target object to a specific location (e.g., a circular chamber of the gantry 110). The gantry 110 may support the radiation generator 108 and the detector 109. In some embodiments, the gantry 110, or a part thereof, may rotate around a rotation axis, thereby enabling the radiation generator 108 and the detector 109 to rotate around the target object. The radiation generator 108 may emit rays toward the target object. Typical rays may include an X-ray, neutrons, protons, heavy ions, or the like, or any combination thereof. The CT device may scan the target object by emitting rays from the radiation generator 108, and may obtain scanning data. During the scanning, the rays may penetrate the target object, and CT image data may be generated after the rays are detected by the detector 109.

As an example, the radiation generator 108 may include an X-ray tube. The detector 109 may be have the shape of an arc. In some embodiments, the detector 109 may be a single-row detector or a multi-row detector. The multi-row detector may refer to a detector including multiple rows of detection units along the Z direction. In some embodiments, the detector 109 may include a plurality of channels arranged along the circumferential direction of the chamber of the gantry 110, each of which may receive X-rays of particular angles. The X-ray tube may rotate around the rotation axis of the gantry 110. During the CT scanning, a focus position of the X-ray tube may offset from an initial position due to heat generated by the X-ray tube. In some embodiments, when the CT data acquisition device scans air and a human body, respectively, in different scans corresponding focus positions of the X-ray tube may be different, which may lead to an error in the response of the detector 109. If air scan data containing the error is used to process human scan data to reconstruct an image, artifacts may occur. A response of the detector 109 may represent the intensity of a beam (X-ray) detected by the detector 109. In some embodiments, the focus position may be obtained through measurements. In some embodiments, a first focus position may be determined by the focus position tracker 104 based on response signals detected by one or more detection units of the detector 109. As used herein, a response signal may refer to a signal detected by, e.g., the detector 109. In some embodiments, a channel of the detector 109 may be operably coupled to one or more detection units (e.g., a detection unit column illustrated in FIG. 2) so as to receive X-rays of particular angles incident on the one or more detector units.

The high voltage generator 102 may generate high voltage or heavy current. In some embodiments, the high voltage or the heavy current generated by the high voltage generator 102 may be transmitted to the radiation generator 108 for generating rays. The controller 103 may be associated with the data acquisition device 101, the high voltage generator 102, the focus position tracker 104, and/or the data processing device 105. In some embodiments, the controller 103 may control the data acquisition device 101 to scan a target object when the focus of the X-ray tube is located at different focus positions. For example, the controller 103 may control the radiation generator 108 and the detector 109 to rotate around the Z axis. In some embodiments, the controller 103 may control the data processing device 105 to perform data or image processing. As another example, the controller 103 may control the data processing device 105 to retrieve response signals from the storage 106, and reconstruct a CT image based on the response signals. In some embodiments, the controller 103 may control the data processing device 105 to acquire response signals directly from the detector 109, and reconstruct a CT image based on the response signals.

The controller 103 may be a control element or a device. For example, the controller 103 may be a microcontroller unit (MCU), a central processing unit (CPU), a programmable logic device (PLD), an application specific integrated circuits (ASIC), a single chip microcomputer (SCM), a system on a chip (SoC), etc.

The focus position tracker 104 may process and analyze input data to generate a processing result. For example, the focus position tracker 104 may process and analyze a parameter of the X-ray (e.g., the X-ray intensity) detected by the detector 109 to determine a focus position of the radiation generator 108. When the radiation generator 108 is an X-ray tube, the focus position tracker 104 may determine a focus position of the X-ray tube. During a CT scanning, the focus position tracker 104 may acquire response signals detected by the detector 109, determine a focus position of the X-ray tube based on the response signals, and store the response signals and the corresponding focus position in, e.g., the storage 106.

In some embodiments, the focus position tracker 104 may be implemented on a server, or a server group. The server group may be centralized, for example, a data center. The server group may also be distributed, for example, a distributed system. The focus position tracker 104 may be implemented on a cloud server, a file server, a database server, an FTP server, an application server, a proxy server, a mail server, or the like, or any combination thereof. The focus position tracker 104 may be local or remote. In some embodiments, the focus position tracker 104 may include a storage device for storing data (e.g., the X-ray intensity detected by the detector 109, etc.) collected by the data acquisition device 101, programs that the focus position tracker 104 operates, and/or various data generated during operation of the focus position tracker 104. The focus position tracker 104 may access information (e.g., a correction table) stored in the storage device during the operation.

The data processing device 105 may perform data processing, including, e.g., image processing. For example, during an air scan or the scanning of a patient, the data processing device 105 may process response signals detected by the detector 109 (or referred to as detector responses) corresponding to different focus positions, and may calibrate focus position offsets. Different focus positions and the detector responses corresponding to the different focus positions may be obtained by the focus position tracker 104 and may be stored in the storage 106. The data processing device 105 may access the storage 106 to acquire different focus positions and the detector responses corresponding to the different focus positions, and may process the acquired focus positions and detector responses. As another example, the data processing device 105 may determine response signals of the detector 109 by calculation, and may reconstruct an image based on the response signals. In some embodiments, the data processing device 105 may receive data from the storage 106 or an external data source, and may process the received data. The external data source may include one or more kinds of a hard disk, a USB storage, an optical disk, a flash memory, a cloud disk, etc.

The data processing device 105 may including one or more processing elements, such as a central processing unit (CPU), a digital signal processor (DSP), a graphics processing unit (GPU), etc. In some embodiments, the data processing device 105 may also be a specialized processing element or device with a particular function. The data processing device 105 may be a local device, such as a console, a desktop computer, a local server, a cloud server with a data/image processing function, etc. The data processing device 105 may transmit a processing result (e.g., a reconstructed CT image) to the storage 106.

The storage 106 may store information. The information may include scan data (e.g., detector response), a focus position corresponding to the scan data, a reconstructed image, a parameter input by a user, a data processing algorithm, or the like. The information stored in the storage 106 may be in the form of text, digits, audio, an image, or the like, or a combination thereof. In some embodiments, the storage 106 may store data (e.g., a parameter of X-ray detected by the detector 109, such as the X-ray intensity) collected from the CT device, programs the focus position tracker 104 operates, and various data generated during the operations of the focus position tracker 104. The focus position tracker 104 may access information (e.g., a mapping table) stored in the storage device during the operations. The storage 106 may also store instructions or codes executed by the data processing device 105 and/or the controller 103. When the data processing device 105 and/or the controller 103 execute the codes, the data processing device 105 may be caused to execute one or more functions of the imaging system 100 disclosed in the present disclosure.

The storage 106 may include but not limited to various types of storage devices, such as a solid-state disk, a mechanical hard disk, a universal serial bus (USB), flash, a secure digital (SD) memory card, an optical disk, a random-access memory (RAM), a read-only memory (ROM), etc. In some embodiments, the storage 106 may be an internal storage device of the system, an external storage device of the system, a network storage device outside the system (e.g., a storage of a cloud storage server, etc.), or the like.

Components in the imaging system 100 may be connected in wired or wireless manner. In some embodiments, the components in the imaging system 100 may be connected via a network. The network may include a local area network, a wide area network, a public network, a private network, a wireless local area network, a virtual network, a metropolitan area network, a public switched telephone network, or the like, or any combination thereof. For example, a network may use WIFI, Bluetooth, ZigBee, and/or other protocols to communicate. In some embodiments, the network may include a variety of network access points, for example, a wired or wireless access point, a base station or a network exchange point, or the like, or a combination thereof. Through an access point, a data source may be connected to the network and send information via the network.

In some embodiments, the imaging system 100 may also communicate with an external device (e.g., a database, a terminal, an input/output interface, etc.). In some embodiments, the high voltage generator 102 in the imaging system 100 may be included in the data acquisition device 101.

Figure 2:
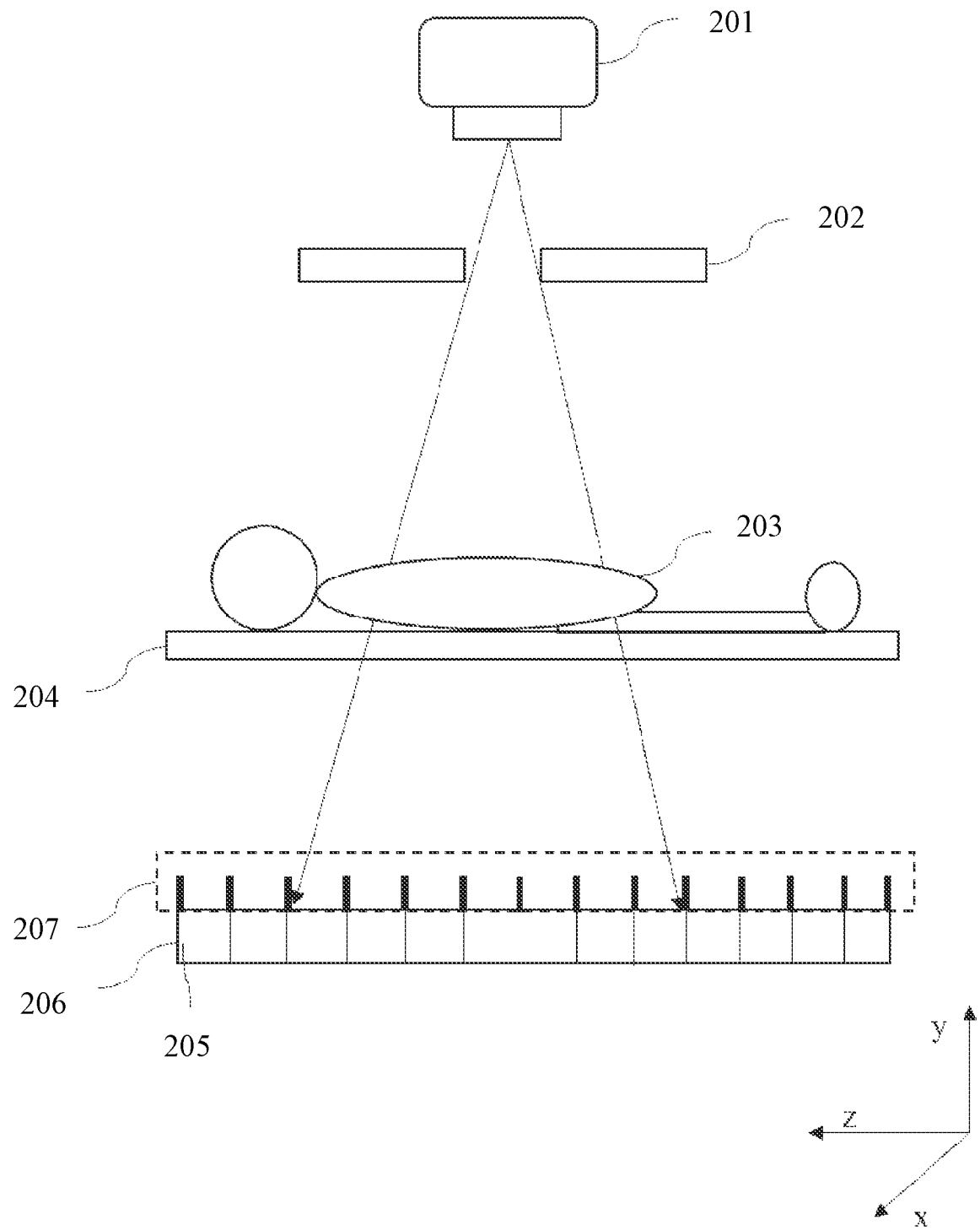
FIG. 2 is a schematic diagram illustrating an exemplary data acquisition device according to some embodiments of the present disclosure.

FIG. 2 is a schematic diagram illustrating an exemplary data acquisition device according to some embodiments of the present disclosure. As an example, the data acquisition device 101 may be a CT scanner. The CT scanner may include an X-ray tube 201, a front collimator 202, a detector 206, a post collimator 207, and a scanning table 204. The X-ray tube 201 may generate X-ray, which may pass through the front collimator 202, pass through a scan object 203

(e.g., air, a phantom, or a patient), and impinge on the detector 206. The front collimator 202 may control a width of the X-ray beam in z direction shown in FIG. 2, so as to determine the thickness of a scan layer. The detector 206 may include a detection unit array (including, for example, a detection unit 205). As shown in FIG. 2, detection units arranged along an x direction may be referred to as a detection unit column, and detection units arranged along the z direction may be referred to as a detection unit row. The radiation intensity of an X-ray beam received by the detector 206 may relate to the attenuation of the X-ray beam when passing through the scan object 203. Each detection unit of the detector 206 may generate a separate electric signal. The separate electric signal may represent a measured value of the beam received by each detection unit. Imaging may be achieved by obtaining the measured values from all of the detection units, respectively. The post collimator 207 may decrease the interference of scattered rays on the detector 206. The post collimator 207 may be mounted above the detector 206, and be in a position close to the upper surface of the detector 206. The post collimator 207 may also be mounted on the upper surface of the detector 206.

During a CT scanning, an X-ray tube rotation shaft may thermally expand due to heat accumulation, resulting in a focus position offset or shift, which in turn may affect the imaging process. For example, the focus of the X-ray tube 201 may be at a first focus position during the scanning of a reference object and at a second focus point during the scanning of a target object. If the first focus position is different from the second focus position, the reconstructed image of the target object may be affected. The system and method described in the present disclosure may be used to mitigate or eliminate adverse effects caused by the offset between the first focus position and the second focus position. The reference object may include air, a phantom, etc. The phantom may be a water phantom, an organic glass phantom, etc. The target object may include a patient, a phantom, etc.

Figure 3:
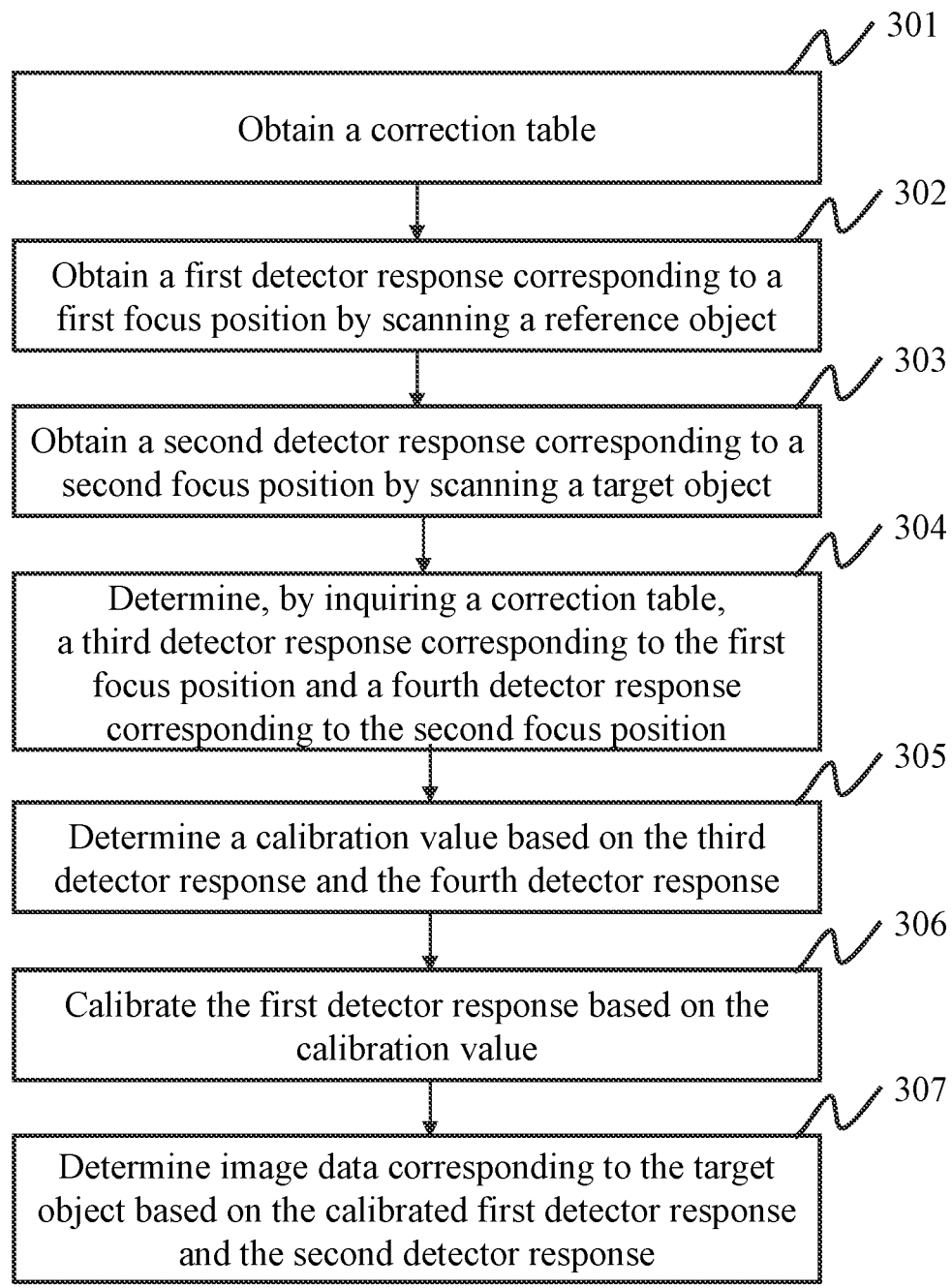
FIG. 3 is a flowchart illustrating an exemplary process for calibrating a focus offset according to some embodiments of the present disclosure.

FIG. 3 is a flowchart illustrating an exemplary process for calibrating a focus position offset according to some embodiments of the present disclosure. In 301, a correction table may be obtained. In some embodiments, during the scanning of a reference object, the correction table may record the correspondence between different focus positions of the X-ray tube and detector responses. The reference object may include air, a phantom, etc. The phantom may be a water phantom, an organic glass phantom, etc. The following description is made with reference to a reference object of air for illustration purposes, and not intended to limit the scope of the present disclosure. In some embodiments, the imaging system 100 may obtain a correction table from one or more external devices (e.g., a database, a terminal, etc.), or an internal storage device or element (e.g., the storage 106). In some embodiments, the correction table may be input by a user. In some embodiments, the imaging system 100 may scan the reference object using the data acquisition device 101, acquire a plurality of detector responses and the corresponding focus positions, and generate a correction table. Merely by way of example, when the data acquisition device 101 scans air or a phantom, the focus position tracker 104 may obtain focus positions, and record the focus positions and corresponding detector responses in the correction table. In some embodiments, one or more focus positions in the present disclosure may be acquired by the focus position tracker 104 using devices or methods illustrated in FIGS. 4 through 12. For example, the focus position tracker 104 may determine a focus position according to a response signal detected by the detector. In some embodiments, the focus positions may be determined in other manners. If the correction table already exists, the imaging system 100 may skip the operation of acquiring a correction table.

In 302, a first detector response corresponding to a first focus position may be acquired by scanning a reference object. The reference object herein may be the same as or different from the reference object used for determining the correction table. For example, the reference object used for determining the correction table may be a phantom, and the reference object herein may be a phantom or air. Merely by way of example, the data acquisition device 101 may perform an air scan (or referred to as air calibration) before scanning a human body, and acquire a first detector response of the air calibration. The first detector response may correspond to a first focus position. The first focus position may refer to a focus position of the X-ray tube 201 when the data acquisition device 101 scans a reference object. In some embodiments, during the scanning of the reference object, the focus position tracker 104 may obtain the first response signal of the detector, and determine the first focus position corresponding to the first response signal.

In 303, a second detector response corresponding to a second focus position may be acquired by scanning a target object. The target object may be a patient. The data acquisition device 101 may scan a certain part (e.g., an organ, such as a lung, a kidney, etc.) or a whole body of the patient, and acquire a second detector response. The second detector response may correspond to a second focus position. The second focus position may refer to a focus position of the X-ray tube 201 when the data acquisition device 101 scans a patient. In some embodiments, during the scanning of a patient, the focus position tracker 104 may acquire the second response signal of the detector, and determine the second focus position corresponding to the second response signal.

In 304, a third detector response corresponding to the first focus position and a fourth detector response corresponding to the second focus position may be determined by consulting the correction table. In some embodiments, the correction table may include the first focus position and/or the second focus position. The imaging system 100 may retrieve the third detector response corresponding to the first focus position and/or the fourth detector response corresponding to the second focus position from the correction table. In some embodiments, the correction table does not include the first focus position and the second focus position. The imaging system 100 may determine the third detector response corresponding to the first focus position and/or the fourth detector response corresponding to the second focus position using one or more processing techniques. The one or more processing techniques may include interpolation, linear fitting, non-linear fitting, or the like.

In 305, a calibration value may be determined based on the third detector response and the fourth detector response. In some embodiments, the calibration value may be a ratio, a product, a difference value, or a result of a power exponent function, or the like. The calibration value may be obtained by performing an operation on the third detector response and/or the fourth detector response. In some embodiments, the calibration value may be a difference value between the fourth detector response and the third detector response. In some embodiments, the calibration value may be a ratio of the fourth detector response to the third detector response.

In 306, the first detector response may be calibrated based on the calibration value. In some embodiments, the data processing device 105 may calibrate the first detector response based on the calibration value. For example, when the calibration value is a difference value between the fourth detector response and the third detector response, the data processing device 105 may generate a calibrated first detector response by adding the difference value to the first detector response. As another example, when the calibration value is a ratio of the fourth detector response to the third detector response, the data processing device 105 may generate a calibrated first detector response by multiplying the ratio by the first detector response. In some embodiments, the calibration value may be generated in other manners. Moreover, a conversion may be performed considering a relationship between the scanned objects corresponding to the correction table and the first focus position, respectively.

In 307, image data of the target object may be determined based on the calibrated first detector response and the second detector response. The data processing device 105 may determine the image data of the target object based on the calibrated first detector response and the second detector response. The data processing device 105 may reconstruct an image based on the imaging data. Exemplary CT reconstruction algorithms may include a filtered back protrusion reconstruction algorithm, a Radon inversion algorithm, a unary function Hilber transform algorithm, an iterative reconstruction algorithm, or the like.

Merely for illustration purposes, the imaging system 100 may determine a correction table. The correction table may record a plurality of detector responses Detresp n (n=1, 2, 3 . . . ) and a plurality of focus positions Sp n (n=1, 2, 3 . . . ) corresponding to the plurality of detector responses Detresp n (n=1, 2, 3 . . . ), respectively. When the data acquisition device 101 scans a first reference object, the focus positions Sp n and the corresponding detector responses Detresp n may be recorded in the correction table. When the data acquisition device 101 scans a second reference object, a first detector response Detresp_sp_obj corresponding to a focus position Sp_obj may be obtained. The second reference object may be the same as or different from the first reference object. For example, the first reference object may be air, and the second reference object may be a phantom. As another example, the first reference object may be a phantom, and the second reference object may be air. As a further example, the first reference object may be air, and the second reference object may also be air. As still a further example, the first reference object and the second reference object may be phantoms of different materials. When the data acquisition device 101 scans a patient, a second detector response Detresp_sp_raw corresponding to a focus position Sp_raw may be obtained. By consulting the correction table and/or performing an interpolation, the data processing device 105 may obtain a third detector response Detresp_sp_obj_table corresponding to the focus position Sp_obj in the correction table, and a fourth detector response Detresp_sp_raw_table corresponding to the focus position Sp_raw in the correction table. Based on the detector response Detresp_sp_raw_table and the detector response Detresp_sp_obj_table, the data processing device 105 may determine a calibration value D according to Equation (1):

$$D = \text{Detresp}\_sp\_\text{raw\_table} - \text{Detresp}\_sp\_\text{obj\_table}. \quad (1)$$

A calibrated first detector response new Detresp_sp_obj may be determine according to Equation (2):

$$\text{new Detresp}\_sp\_\text{obj} = D + \text{Detresp}\_sp\_\text{obj}. \quad (2)$$

The data processing device 105 may obtain image data corresponding to the target object based on the calibrated first detector response and the second detector response, and reconstruct an image based on the image data.

Merely for illustration purposes, the imaging system 100 may determine a correction table. When the data acquisition device 101 scans a first reference object, detector responses Detresp n (n=1, 2, 3 . . . ) and corresponding focus positions Sp n (n=1, 2, 3 . . . ) may be recorded in the correction table. When the data acquisition device 101 scans a second reference object, a first detector response Detresp_sp_obj corresponding to a focus position Sp_obj may be obtained. When the data acquisition device 101 scans a patient, a second detector response Detresp_sp_raw corresponding to a focus position Sp_raw may be obtained. By consulting the table and/or performing an interpolation, the data processing device 105 may obtain a third detector response Detresp_sp_obj_table corresponding to the focus position Sp_obj, and a fourth detector response Detresp_sp_raw_table corresponding to the focus position Sp_raw. According to the detector response Detresp_sp_raw_table and the detector response Detresp_sp_obj_table, the data processing device 105 may determine a calibration value R according to Equation (3):

$$R = \text{Detresp}\_sp\_\text{raw\_table} / \text{Detresp}\_sp\_\text{obj\_table}. \quad (3)$$

A calibrated first detector response may be determined according to Equation (4):

$$\text{new Detresp}\_sp\_\text{obj} = R \cdot \text{Detresp}\_sp\_\text{obj}. \quad (4)$$

The data processing device 105 may obtain image data corresponding to the target object based on the calibrated first detector response and the second detector response, and reconstruct an image based on the image data.

In some embodiments, one or more focus positions described in the present disclosure may be tracked or determined by a collimator. The collimator may be used to determine a focus position offset of the X-ray tube 201 along the z direction as shown in FIG. 2. The collimator described in the present disclosure may track the focus position of the X-ray tube when a reference object and a target object are scanned, respectively so that errors introduced by an offset of the focus position may be corrected by eliminating or mitigating artifacts caused by the offset of the focus position. The collimator may include one or more openings. The collimator may have a certain width in a first direction (e.g., the z direction shown in FIG. 2), and a certain length in a second direction (e.g., the x direction shown in FIG. 2). The opening may have a plurality of opening widths in the first direction. An opening width corresponding to at least one end of the opening may be smaller than an opening width corresponding to a middle section of the opening.

Figure 12:
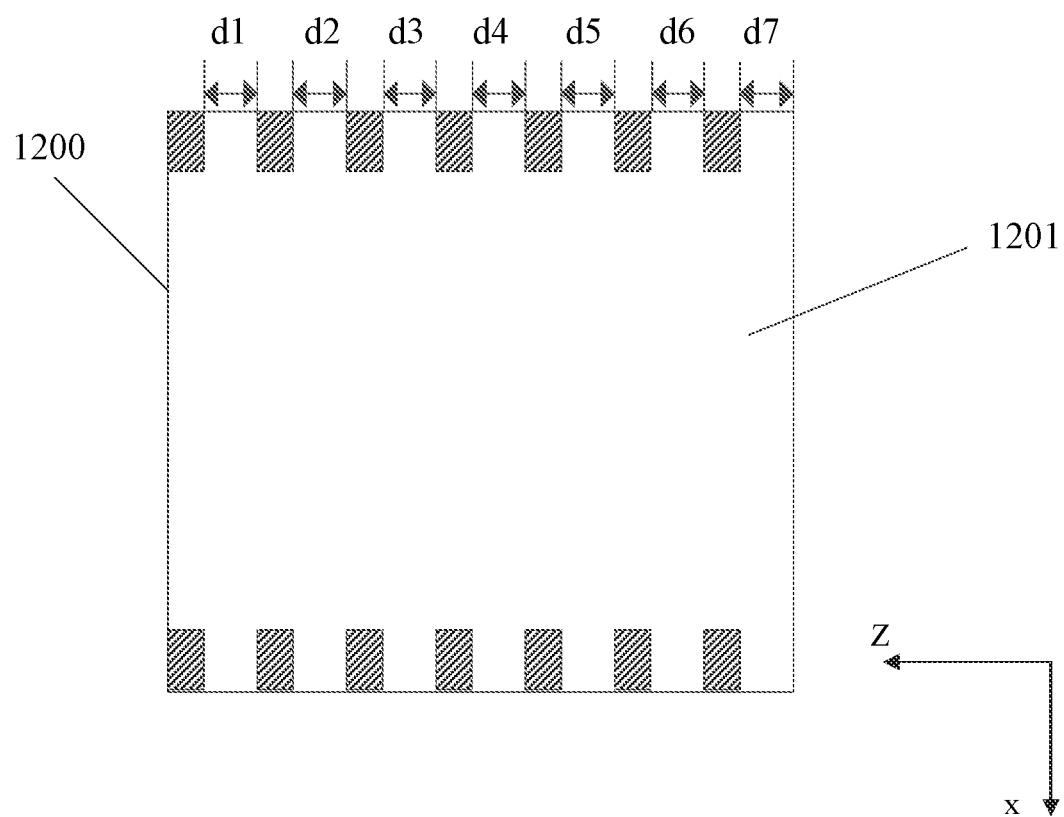
FIG. 12 is a top view of another collimator according to some embodiments of the present disclosure.

The opening width may refer to a width of the opening in the first direction. In some embodiments, opening widths corresponding to different sections of the opening or the collimator along the second direction may be different. For example, referring to FIGS. 4A-4F and FIGS. 5A-5F, the collimator may have one opening. An opening at at least one end of the collimator in the length direction (i.e., the x direction) may have an opening width smaller than that of an opening within a middle section of the collimator in the length direction. As used herein, the middle section may refer to a position or a portion including and/or in the vicinity of a center of the collimator (e.g., 530a in FIG. 5A) relative to the left end and the right end of the collimator. For instance, the middle section of the collimator may be a portion of, e.g., half, a third, a fourth, a fifth, of the entire length of the collimator in the middle of the collimator along the length direction of the collimator. In some embodiments, the collimator may have a plurality of openings. The opening width may refer to a width of one opening in the first direction, or a sum of the widths of the plurality of openings in the first direction. For example, referring to FIG. 11, a collimator 1100 has three openings 1101, 1102, and 1103. The opening width may refer to a width of the opening 1101, 1102, or 1103. The opening width may also refer to a sum of widths of the opening 1101, 1102, and 1103. In some embodiments, a single opening, e.g., an opening 530a in FIG. 5A, may be continuous in its width direction (i.e., the first direction). In some embodiments, a single opening, e.g., an opening 1201 in FIG. 12, may be discontinuous in its width direction, and the opening width may be a sum of several discontinuous widths. Referring to FIG. 12, a collimator 1200 may have an opening 1201. The opening width corresponding to an end of the opening 1201 in the second direction (i.e., the x direction) may be discontinuous. The opening width corresponding to the end of the opening 1201 in the second direction may be Σdi, where Σ represents a summation operator, di represents a distance between two adjacent protrusions, and i=1, 2, . . . , 7.

In some embodiments, a collimator may be made of a material with a large density (e.g., plumbum) for shielding X-ray.

In some embodiments, the collimator described in the present disclosure may take the form of a blade. For instance, the front collimator 202 may include a blade. At least one end of the blade along the second direction (i.e., the x direction) may have one or more protrusions. The protrusions may protrude into an opening included in the blade. A gap may be formed between two protrusions. The one or more protrusions may be formed as one-piece with or an integral part of the blade, or removably attached to the blade. FIGS. 4A to 4F are top views of exemplary collimators according to some embodiments of the present disclosure. The x direction and the z direction shown in FIG. 4A may correspond to the x direction and the z direction shown in FIG. 2, respectively. The blade may include a pair of blocks disposed opposite to each other (e.g., a block 440 and a block 450), which may define an opening (e.g., an opening 430a, 430b, 430c, 430d, 430e, or 430f). The blocks may shift along the first direction (e.g., the z direction of FIG. 4A) to determine a width of the opening.

In some embodiments, at least one of the blocks (e.g., a block 440 and/or a block 450) may have a protrusion (e.g., protrusions 421, 422, 423, or 424) at at least one end in the second direction (e.g., the x direction shown in FIG. 4A), and the protrusion may protrude into the opening, and thus an opening at at least one end of the blade in the second direction may have an opening width smaller than that of an opening within a middle section of the blade in the second direction. For example, a cross-section of the block 440 (or the block 450) in the x-z plane may be of a concave shape, an "L" shape, or the like. In some embodiments, an opening width corresponding to a section of an opening of the collimator in the second direction may be referred to as a width at a position of the opening along the second direction formed by blocks arranged opposite to each other.

Figure 4A:
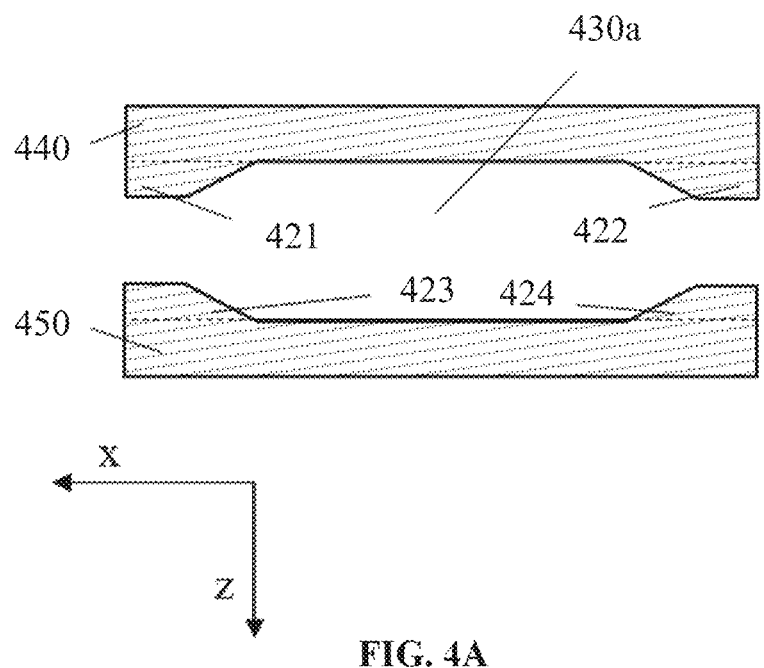
FIGS. 4A to 4F are top views of exemplary collimators according to some embodiments of the present disclosure.

For example, as shown in FIG. 4A, both ends of blocks 440 and 450 in the second direction (e.g., the x direction shown in FIG. 4A) may extend into the opening 430a, forming four protrusions (e.g., the protrusions 421, 422, 423, or 424).

Figure 4B:
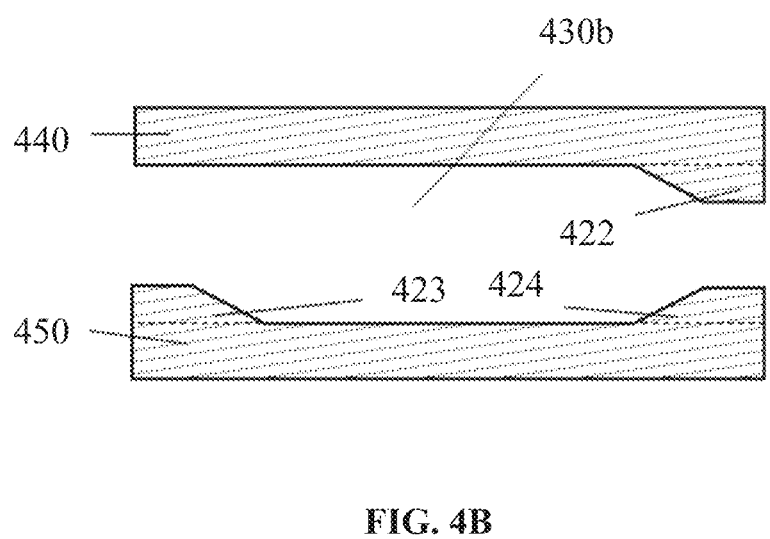

As another example, as shown in FIG. 4B, one end of the block 440 (or the block 450) in the second direction may extend into the opening 430b, forming a protrusion (e.g., the protrusion 422). Both ends of the block 450 (or the block 440) in the second direction may extend into the opening 430b, forming two protrusions (e.g., the protrusions 423, or 424).

Figure 4C:
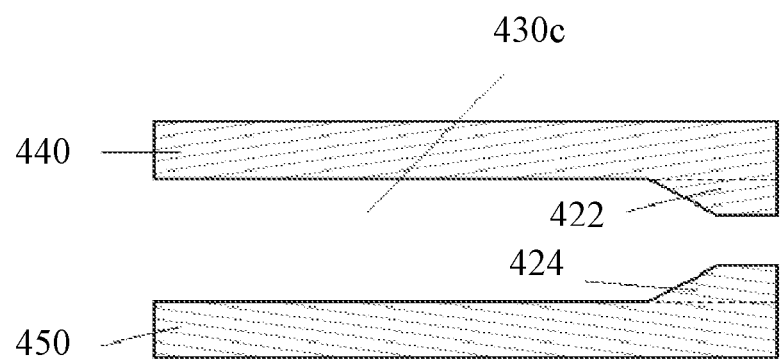

As another example, as shown in FIG. 4C, the ends of the block 440 and the block 450 at a same side in the second direction may extend into the opening 430c, respectively, each forming one protrusion (e.g., the protrusions 422 and 424).

Figure 4D:
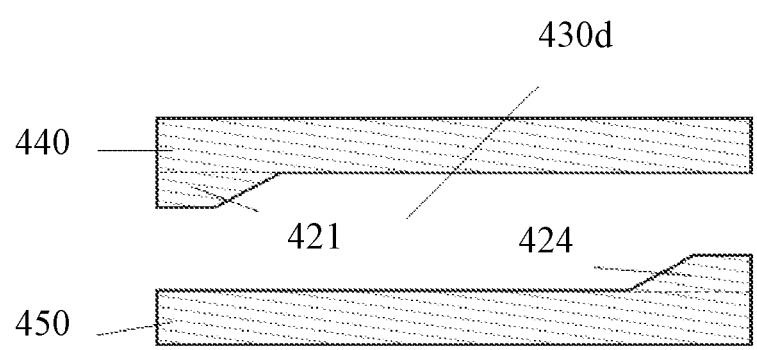

As another example, as shown in FIG. 4D, an end of the block 440 and an end of the block 450 on different sides in the second direction may extend into the opening 430d, respectively, each forming one protrusion (e.g., the protrusions 421 and 424).

Figure 4E:
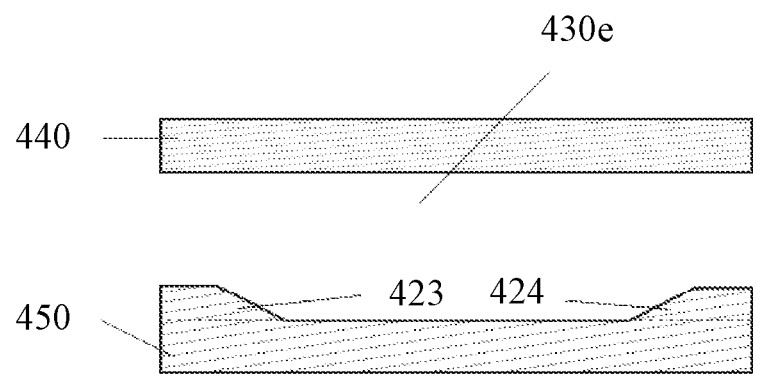

As a further example, as shown in FIG. 4E, both ends of the block 450 (or the block 440) in the second direction may extend into the opening 430e, forming two protrusions (e.g., the protrusions 423 and 424).

Figure 4F:
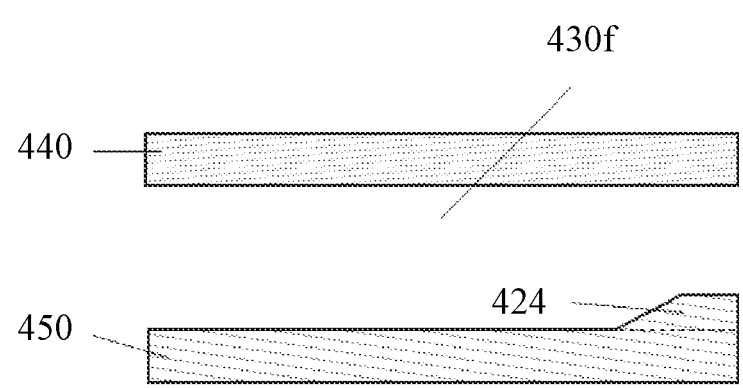

As still a further example, as shown in FIG. 4F, one end of the block 450 (or the block 440) in the second direction may extend into the opening 430f, forming one protrusion (e.g., the protrusion 424).

In some embodiments of the present disclosure, the collimator may have a substantially rectangular or square opening. At least one corner of the opening may include a protrusion that may protrude into the opening. FIG. 5A to FIG. 5F are top views of exemplary collimators according to some embodiments of the present disclosure. The collimators in FIGS. 5A through 5F may include a body of a same shape, for example, illustrated as the body 510. The x direction and z direction shown in FIG. 5A may correspond to the x direction and z direction shown in FIG. 2, respectively. The blade may include a plurality of openings with different widths (see, e.g., FIG. 11) along the first direction (e.g., the z direction shown in FIG. 5A). Among the plurality of openings of different widths, at least one of the plurality of openings may have a different width along the second direction (e.g., the x direction shown in FIG. 5A) relative to other openings of the plurality of openings. Further, a middle section of at least one of the openings in the second direction may have a greater width than that of at least one end in the second direction.

As shown in FIGS. 5A-5F, for an opening having a width changing along the second direction (e.g., the x direction shown in FIG. 5A), at least one end of the blade in the second direction may extend into the opening to form one or more protrusions (e.g., protrusions 521, 522, 523 and/or 524), and thus an opening within a middle section of the blade in the second direction may have an opening width greater than that of an opening at at least one end of the blade in the second direction. In some embodiments, an opening width corresponding to a section of an opening of the collimator along the second direction may be referred to as a width corresponding to the section of the opening of a plurality of openings along the second direction. The plurality of openings may have different widths in the first direction.

Figure 5A:
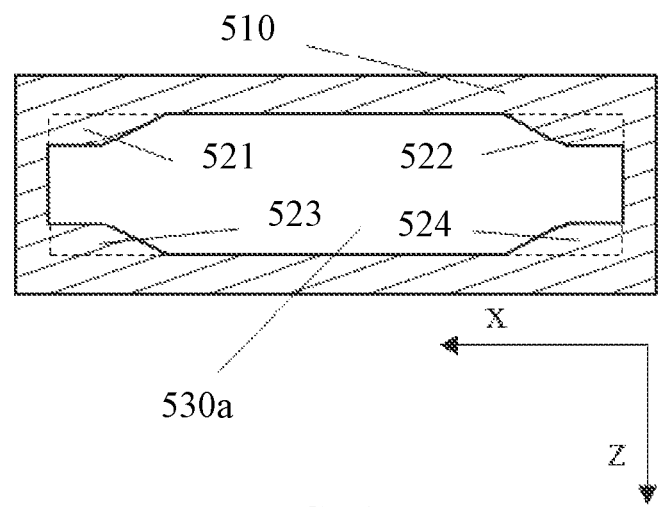
FIGS. 5A to 5F are top views of exemplary collimators according to some embodiments of the present disclosure.

For example, as shown in FIG. 5A, both ends of the blade in the second direction may extend into an opening 530a, forming four protrusions (e.g., protrusions 521, 522, 523, and 524).

Figure 5B:
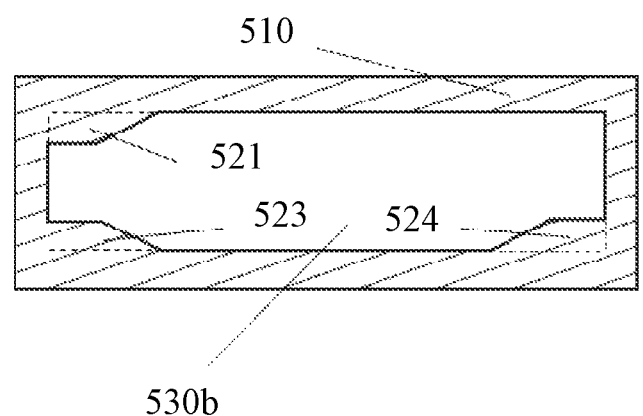

As another example, as shown in FIG. 5B, one end of the blade in the second direction may extend into an opening 530b, forming two protrusions (e.g., protrusions 521 and 523). The other end of the blade in the second direction may extend into the opening 530*b*, forming another protrusion (e.g., a protrusion 524).

Figure 5C:
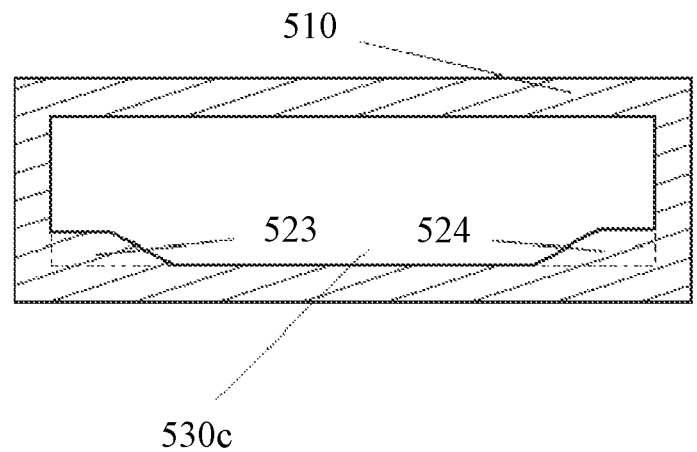
Figure 5D:
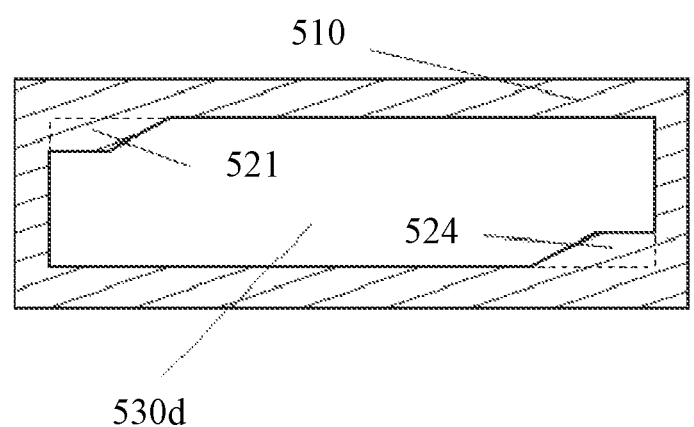

As another example, as shown in FIG. 5C or FIG. 5D, both ends of the blade in the second direction may extend into an opening 530*c* (or 530*d*), forming two protrusions (e.g., protrusions 523 and 524 in FIG. 5C, or protrusions 521 and 524 in FIG. 5D).

Figure 5E:
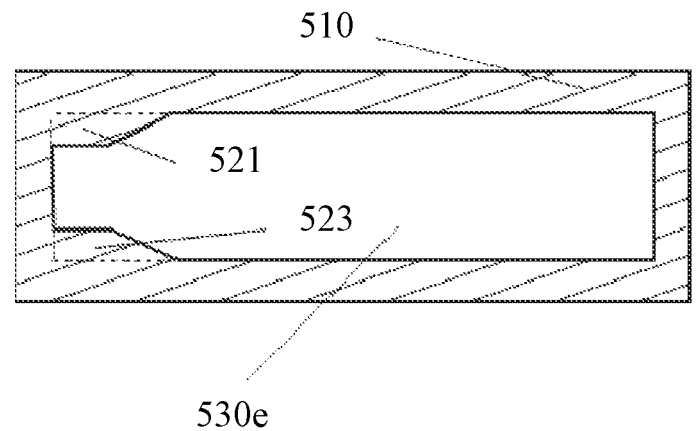

As a further example, as shown in FIG. 5E, one end of the blade in the second direction may extend into an opening 530*e*, forming two protrusions (e.g., protrusions 521 and 523).

Figure 5F:
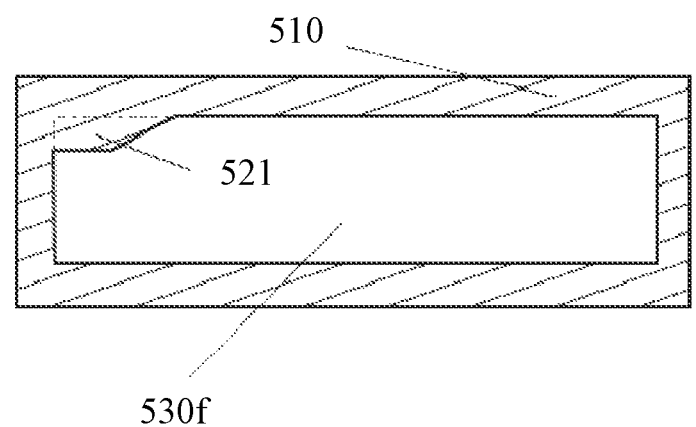

As still a further example, as shown in FIG. 5F, one end of the blade in the second direction may extend into an opening 530*f*, forming a protrusion (e.g., a protrusion 521).

The blades shown in FIGS. 4A-4F and FIGS. 5A-5F may be implemented in the front collimator 202. The protrusions of the blades may shield one or more detection units located around the edges of the detector 206 in the second direction, while leave detection units within a middle section of the detector 206 in the second direction unshielded, thereby improving X-ray efficiency and image quality. When a focus position of the X-ray tube 201 shifts, the intensity of the X-ray impinging on the shielded detection units located around the edges of the detector 206 in the second direction may be reduced. A signal-noise ratio of the beam intensity variation, which may indicate the sensitivity of the beam intensity variation when the focus position is tracked, may be effectively improved due to the protrusions set at at least one corner of the opening of the collimator, thereby improving an accuracy for tracking the focus position. The second direction of the detector 206 may be the same as the second direction of the collimator.

According to some embodiments of the present disclosure, the collimator may include an anti-scatter grid. For instance, the post collimator 207 may include an anti-scatter grid.

Figure 6A:
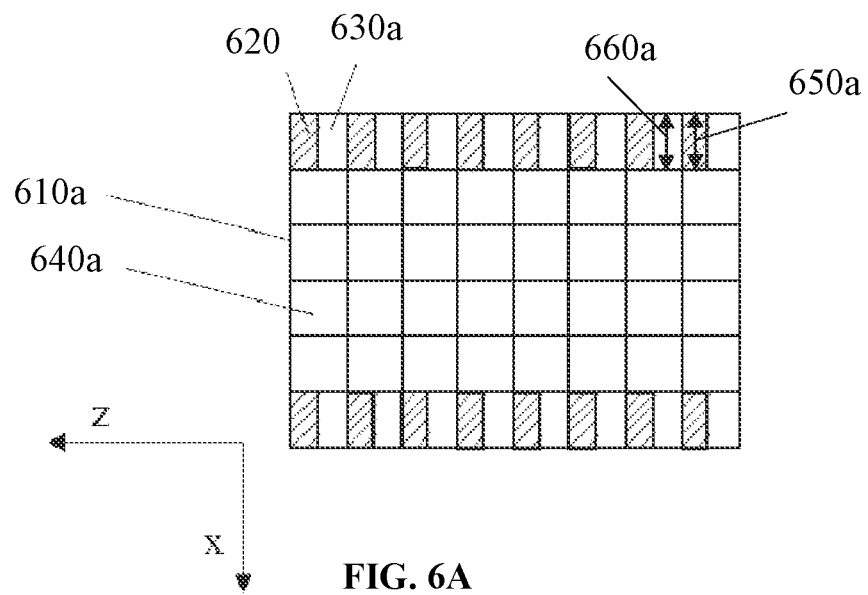
FIGS. 6A to 6C are top views of exemplary collimators according to some embodiments of the present disclosure.
Figure 6B:
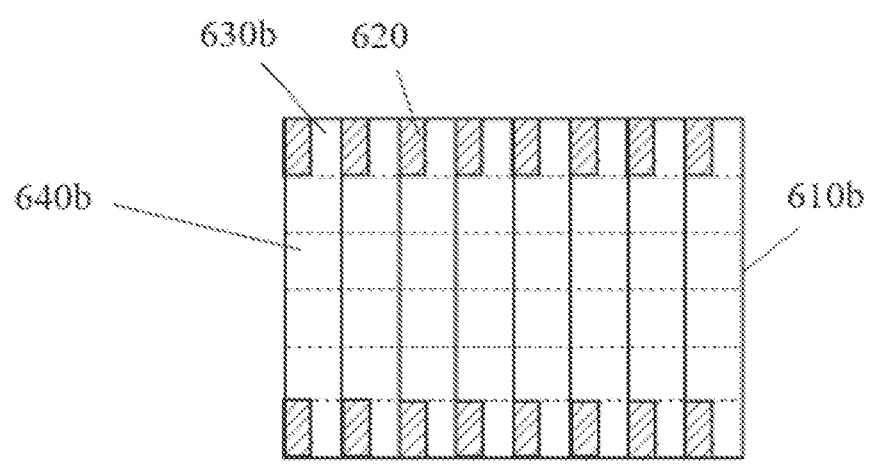
Figure 6C:
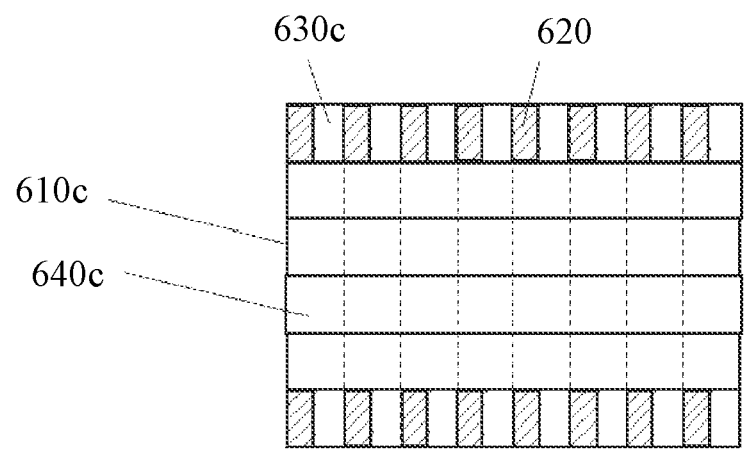

FIG. 6A to FIG. 6C are top views of exemplary collimators according to some embodiments of present disclosure. The x direction and z direction shown in FIG. 6A may correspond to the x direction and z direction shown in FIG. 2, respectively.

As shown in FIG. 6A to FIG. 6C, the anti-scatter grid may include a plurality of sub-openings. Each sub-opening may correspond to one or more detection units of the detector 206. For example, as shown in FIG. 6A, an anti-scatter grid may have a plurality of sub-openings (e.g., sub-openings 630*a* and 640*a*), and each sub-opening may correspond to a detection unit. As another example, as shown in FIG. 6B, an anti-scatter grid may have a plurality of sub-openings (e.g., a sub-opening 630*b*), and each sub-opening may correspond to a column of detection units. As still another example, an anti-scatter grid may have a plurality of sub-openings (e.g., sub-openings 630*c* and 640*c* illustrated in FIG. 6C), and each sub-opening in a beam direction may correspond to a row or a column of detection units or a detection unit.

The anti-scatter grid may include a body (e.g., a body 610*a*, 610*b*, or 610*c*), and a plurality of protrusions (e.g., a protrusion 620). In some embodiments, the lengths of the protrusions (e.g., the protrusion 620) in the second direction (e.g., the x direction shown in FIG. 6A) may be the same as or smaller than the lengths of the sub-openings (e.g., the sub-opening 630*a*) in the second direction. Merely for illustration purposes, as illustrated in FIG. 6A, the length 650*a* of the protrusion 620 may be the same as or smaller than the length 660*a* of the sub-opening 630*a*. The plurality of protrusions may be located on the edges of the body in the first direction (e.g., the z direction shown in FIG. 6A), and the plurality of protrusions may be arranged along the first direction. Due to the presence of the protrusions, an opening including a plurality of sub-openings at at least one end of the anti-scatter grid in the second direction (e.g., 630*a* in FIG. 6A) may have an opening width smaller than that of an opening within a middle section of the anti-scatter grid in the second direction (e.g., 640*a* in FIG. 6A). In some embodiments, an opening width of the collimator in the second direction may refer to a width of an opening of a plurality of sub-openings in the anti-scatter grid along the second direction.

For example, as shown in FIG. 6A, a width of the sub-opening 630*a* in the first direction (i.e., the z direction) may be smaller than a width of the sub-opening 640*a* in the first direction. As shown in FIG. 6B, a width of the sub-opening 630*b* in the first direction (i.e., the z direction) may be smaller than a width of the sub-opening 640*b* in the first direction. As shown in FIG. 6C, a width of the sub-opening 630*c* in the first direction may be smaller than a width of the sub-opening 640*c* in the first direction.

As still another example, as shown in FIG. 6A, a sum of widths of sub-openings at one end of the anti-scatter grid in the second direction (e.g., a sum of opening widths of eight sub-openings in a row along the upper end of the body 610*a*) may be smaller than a sum of widths of sub-openings within a middle section of the anti-scatter grid in the second direction (e.g., a sum of opening widths of eight sub-openings in a row within a middle section of the body 610*a*). Merely for illustration purposes as illustrated in FIG. 6A, the anti-scatter grid may include six rows of sub-openings from the upper end to the lower end, and each row may have eight sub-openings. The total widths of a row of sub-openings at the upper end or the lower end may be smaller than the total widths of any one of the four rows of sub-openings between the upper end and the lower end due to the presence of the protrusions in the sub-openings at both the upper end and the lower end of the anti-scatter grid. The middle section may refer to a position or a portion including and/or in the vicinity of a center of the body 610*a* relative to the upper end and the lower end of the body 610*a*. For instance, the middle section of the collimator may be a portion of, e.g., half, a third, a fourth, a fifth, of the entire length of the collimator in the middle of the collimator along the length direction (i.e., the x direction in FIG. 6A) of the collimator. The sub-openings at the end of the anti-scatter may correspond to a row of detection units. The sub-openings within the middle section of the anti-scatter may correspond to another row of detection units. As shown in FIG. 6B, a sum of widths of sub-openings at one end of the anti-scatter grid in the second direction (e.g., a sum of opening widths of eight sub-openings along the upper end of the body 610*b*) may be smaller than a sum of widths of sub-openings within a middle section of the anti-scatter grid in the second direction (e.g., a sum of opening widths of eight sub-openings within a middle section of the body 610*b*). The sub-openings at the end of the anti-scatter may correspond to a row of detection units. The sub-openings within the middle section of the anti-scatter may correspond to another row of detection units. As shown in FIG. 6C, a sum of widths of sub-openings at one end of the anti-scatter grid in the second direction may be smaller than a sum of widths of sub-openings, including an opening 640*c*, within a middle section of the anti-scatter grid in the second direction. The middle section may refer to a position or a portion including and/or in the vicinity of a center of the body 610*c* relative to the upper end and the lower end of the body 610*c*. The sub-openings at the end of the anti-scatter may correspond to a row of detection units. The sub-openings within the middle section of the anti-scatter may correspond to another row of detection units.

Each protrusion may be used for partially shielding an edge detection unit. An edge detection unit may refer to a detection unit located at an edge of the detector in the second direction. The detector may include multiple edge detector units positioned next to each other along the first direction (i.e., the z direction). For example, the edge detection units may include two rows of detection units of outermost layers of the detector 206 along the x direction, four rows of detection units of outermost layers of the detector 206 along the x direction, or six rows of detection units of outermost layers of the detector 206 along the x direction. In some embodiments, the sizes of the edge detection units in the second direction (also referred to as "x direction") may correspond to the sizes of the protrusions in the second direction. As used herein, "correspond to" may indicate that an edge detection unit may be at least partially shielded by a protrusion in a beam direction. In some embodiments, the second direction may be perpendicular to the first direction. In some embodiments, each protrusion may partially shield an edge detection unit of the edge detection units. For example, each protrusion 620 may shield a left part of an edge detection unit as shown in FIGS. 6A-6C of the edge detection units. In some embodiments, each protrusion may also shield other parts of a detection unit of the edge detection units.

The one or more protrusions may be formed as one-piece with or an integral part of the body, or removably attached to the body. In some embodiments, the protrusions may be directly connected to the body. In some embodiments, the protrusions, or may be attached to the body through a braced structure connected to the body.

The post collimator 207 may include an anti-scatter grid structure shown in any one of FIGS. 6A-6C. A protrusion of the anti-scatter grid may shield a part of an edge detection unit of the detector 206 in the second direction. When a focus position of the X-ray tube 201 shifts, the intensity of the X-ray impinging on the shielded detection units located around the edges of the detector 206 in the second direction may be reduced. A signal-noise ratio of the beam intensity variation may be effectively improved, thereby improving an accuracy for tracking the focus position.

Figure 7:
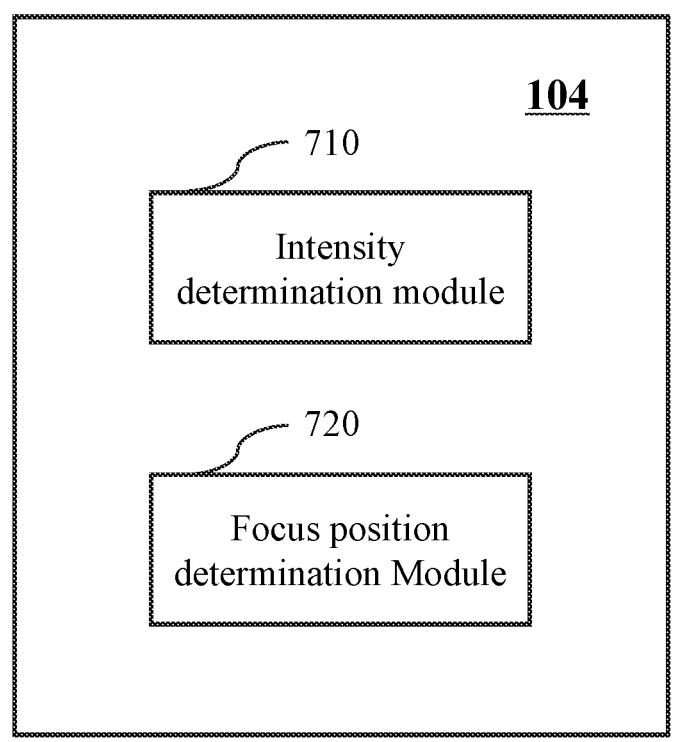
FIG. 7 is a block diagram illustrating an exemplary focus position tracker according to some embodiments of the present disclosure.

FIG. 7 is a block diagram of a focus position tracker 104 according to some embodiments of the present disclosure. In some embodiments, a collimator (e.g., the collimator described in FIGS. 4A-4F, FIGS. 5A-5F or FIGS. 6A-6C) for tracking a focus position of the X-ray tube described in the present disclosure may partially shield edge detection units of the detector 206. When the focus position of the X-ray tube 201 shifts, the X-ray detected by the edge detection units may change accordingly. For instance, the X-ray intensity distribution may be changed. The focus position tracker 104 may include an intensity determination module 710 and a focus position determination module 720 to determine, for example, the X-ray intensity distribution and a focus position. Thus, offsets of the focus position may be determined based on the changes of the X-ray detected by the edge detection units.

The intensity determination module 710 may determine X-ray intensity information. For example, X-ray intensity information may include a first boundary intensity and a second boundary intensity detected by edge detection units, and an X-ray intensity distribution detected by edge detection units. The edge detection units may refer to detection units located at an edge of the detector in the second direction. The X-ray intensity distribution detected by the edge detection units may represent a distribution of detection units that have detected X-ray emitted from the X-ray tube 201, when a focus of the X-ray tube 201 is located at a certain position. The X-ray intensity distribution detected by the edge detection units may also represent a distribution of X-ray intensity detected by each edge detection unit, when a focus of the X-ray tube is located at a certain position. The X-ray intensities detected by edge detection units located at two ends of a same row may be the first boundary intensity and the second boundary intensity of the X-ray intensity distribution, respectively. The boundary may correspond to a farthest detection unit of detection units arranged in the first direction along which the X-ray irradiates.

The focus position determination module 720 may determine a focus position according to the X-ray intensity information. For example, the focus position determination module 720 may determine, according to a geometric relationship, an offset between an initial focus position and an offset focus position based on a first X-ray intensity distribution detected by edge detection units and a second X-ray intensity distribution detected by edge detection units. The first X-ray intensity distribution may correspond to the initial focus position. The second X-ray intensity distribution may correspond to the offset focus position. As another example, the focus position determination module 720 may determine, according to a mapping table, a current focus position (e.g., the offset focus position) of the X-ray tube 201 based on a ratio of a first boundary intensity to a second boundary intensity that are detected by the edge detection units.

Figure 8:
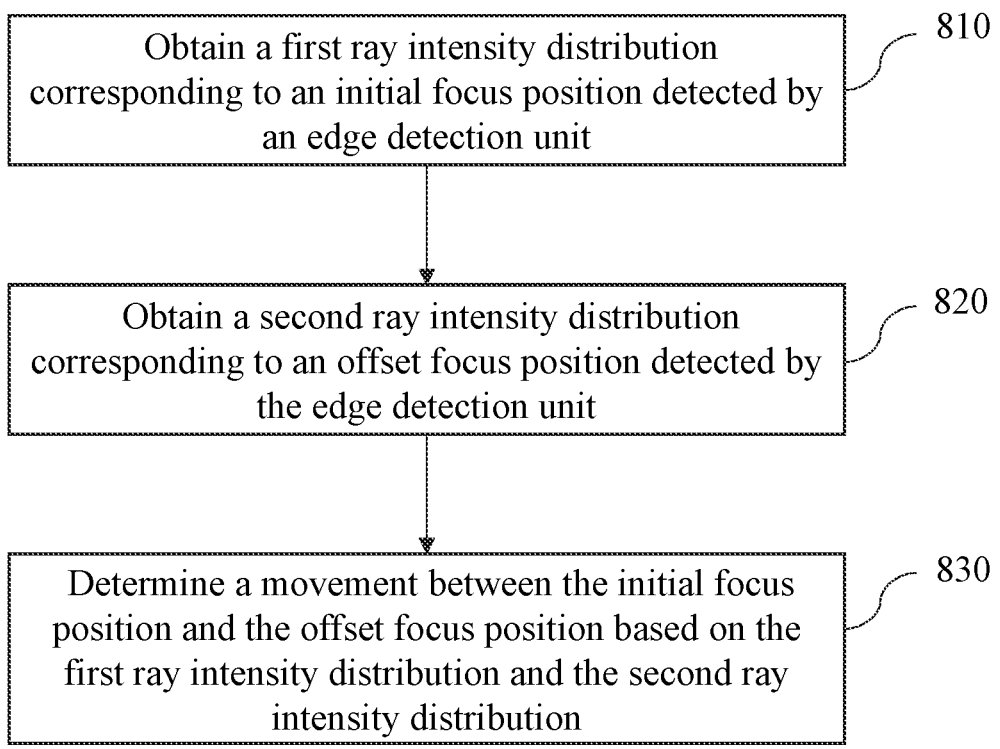
FIG. 8 is a flowchart illustrating an exemplary process for tracking focus positions according to some embodiments of the present disclosure.

FIG. 8 is a flowchart illustrating an exemplary process for tracking a focus position according to some embodiments of the present disclosure. In 810, the intensity determination module 710 may obtain a first X-ray intensity distribution corresponding to the initial focus position of the X-ray tube 201. The first X-ray intensity distribution may be detected by one or more edge detection units. The first X-ray intensity distribution may represent a distribution of detection units that have detected X-ray emitted from the X-ray tube 201, when the focus of the X-ray tube 201 is located at an initial focus position.

In 820, the intensity determination module 710 may obtain a second ray intensity distribution corresponding to the offset focus position of the X-ray tube 201. The second ray intensity distribution may be detected by one or more edge detection units. The second ray intensity distribution may represent a distribution of detection units that have detected X-ray emitted from the X-ray tube 201, when the focus of the X-ray tube 201 is located at an offset focus position.

In 830, the focus position determination module 720 may determine an offset between the initial focus position and the offset focus position based on the first X-ray intensity distribution and the second X-ray intensity distribution. The focus position determination module 720 may determine a first detection unit located at one end of a row of detection units in the first X-ray intensity distribution, and a second detection unit located at the same end of the same row of detection units in the second X-ray intensity distribution. The focus position determination module 720 may determine the offset between the initial focus position and the offset focus position based on a distance between the first detection unit and the second detection unit. The distance between the first detection unit and the second detection unit may refer to a distance between the geometric centers of the two detection units.

The focus position determination module 720 may determine the offset between the initial focus position and the offset focus position according to a geometric relationship between the distance of the two detection units and the offset between the initial focus position and the offset focus position. A current focus position (i.e., the offset focus position) may be obtained.

Figure 9:
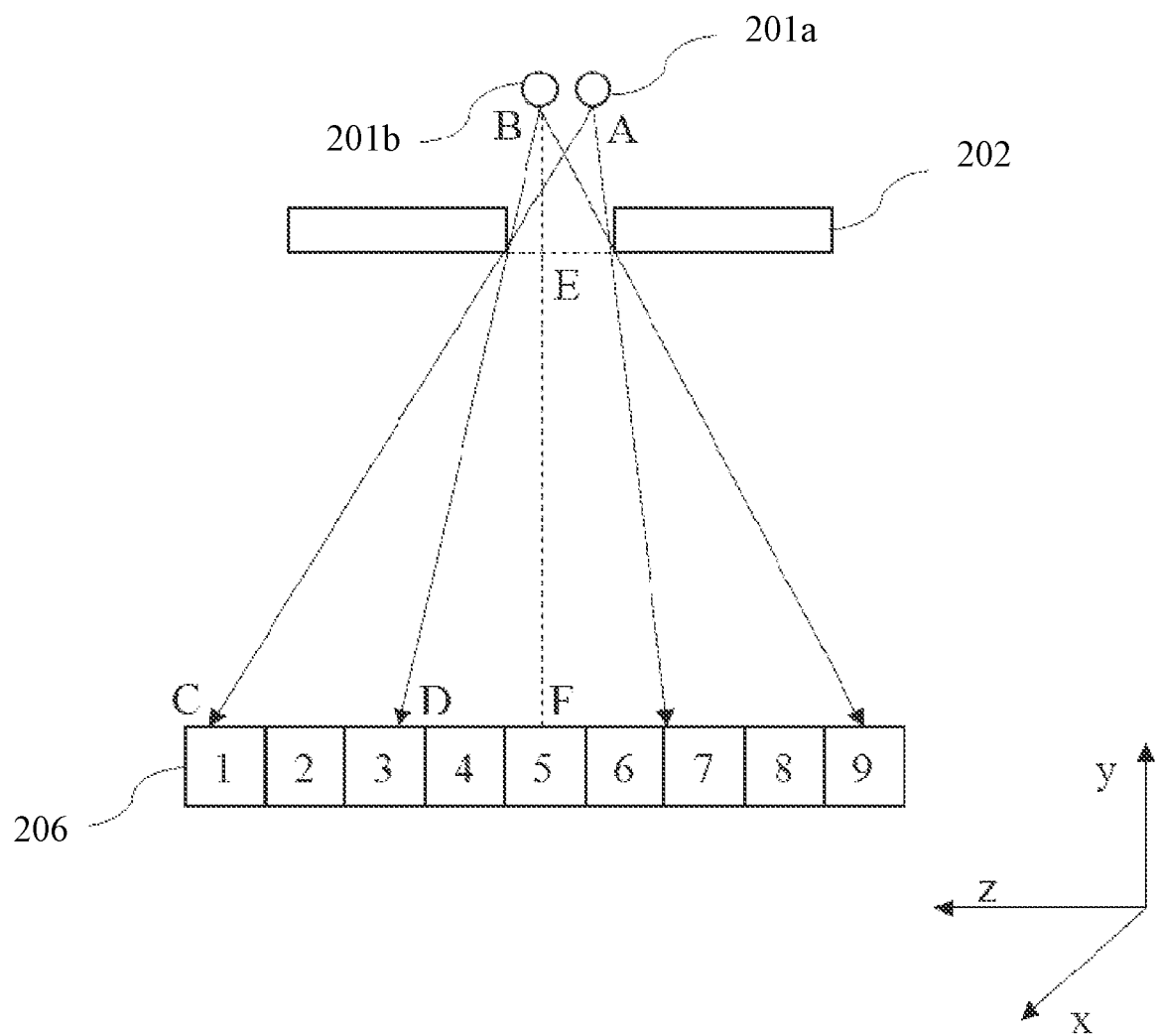
FIG. 9 is an exemplary diagram corresponding to the process for tracking focus positions illustrated in FIG. 8.

Merely by way of example, the x direction, the y direction, and the z direction shown in FIG. 9 may correspond to the x direction, the y direction, and the z direction shown in FIG. 2, respectively. As shown in FIG. 9, detection units 1-9 may constitute a detection unit row of the edge detection units. The first X-ray intensity distribution corresponding to the initial focus position 201a may be associated with detection units 1-7. The second ray intensity distribution corresponding to the offset focus position 201b may be associated with detection units 3-9. Therefore, an offset between the initial focus position 201a and the offset focus position 201b may be determined based on a distance between corresponding detection units associated with the first X-ray intensity distribution and the second X-ray intensity distribution, respectively (e.g., a distance between detection units 1 and 3, a distance between detection units 2 and 4, a distance between detection units 3 and 5, a distance between detection units 4 and 6, etc.). The movement between the initial focus position 201a and the offset focus position 201b may be determined according to Equation (5):

$$AB=(BE \times CD)/EF, \quad (5)$$

where AB may represent the offset between the initial focus position 201a and the offset focus position 201b, BE may represent a distance between the X-ray tube 201 and the front collimator 202, EF may represent a distance between the detector 206 and the front collimator 202, CD may represent a distance between a first detection unit that is located at the boundary in the first direction corresponding to the first X-ray intensity distribution and a second detection unit that is located at the same boundary in the first direction corresponding to the second X-ray intensity distribution.

Figure 10:
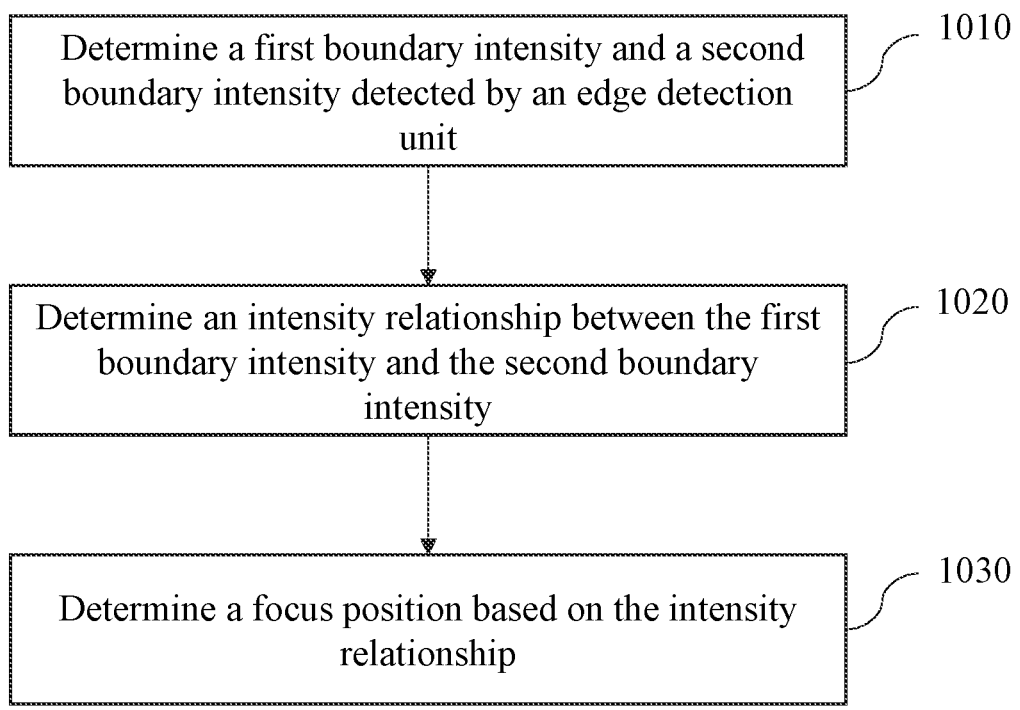
FIG. 10 is a flowchart illustrating another exemplary process for tracking focus positions according to some embodiments of the present disclosure.
Figure 11:
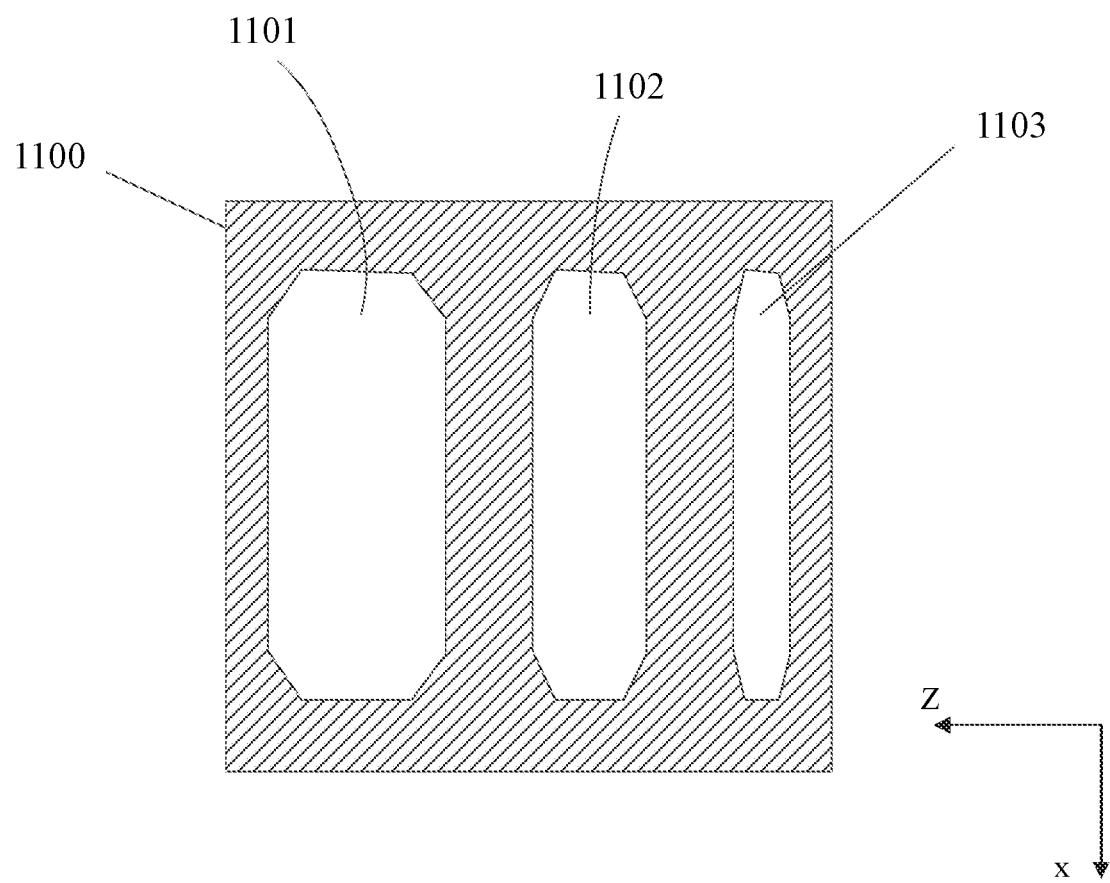
FIG. 11 is a top view of a collimator according to some embodiments of the present disclosure.

FIG. 10 is a flowchart illustrating an exemplary process for tracking a focus position according to some embodiments of the present disclosure. In 1010, the intensity determination module 710 may determine a first boundary intensity and a second boundary intensity that are detected by edge detection units. For example, as shown in FIG. 9, when the X-ray tube 201 is located at a current focus position 201a, the intensity determination module 710 may determine an X-ray intensity (e.g., the first boundary intensity) detected by a detection unit 1 and an X-ray intensity (e.g., the second boundary intensity) detected by a detection unit 7. In 1020, the focus position determination module 720 may determine an X-ray intensity relationship between the first boundary intensity and the second boundary intensity. In this example, the X-ray intensity relationship may include, but are not limited to, an X-ray intensity ratio, or one or more other mathematical relationships. The X-ray intensity ratio may be a ratio of the first boundary intensity to the second boundary intensity, or a ratio of the second boundary intensity to the first boundary intensity. Another exemplary mathematical relationship may be y=kx+z, where x and y may represent one of the first boundary intensity and the second boundary intensity, respectively, and z may be a constant. Other types of relationships may be conceived by those skilled in the art in light of the embodiments of the present disclosure.

In 1030, the focus position determination module 720 may determine a focus position based on the X-ray intensity relationship. In some embodiments, the focus position determination module 720 may determine the focus position according to a mapping table, which may record focus positions and corresponding X-ray intensities. The mapping table may record multiple sets of mapping relationships. A set of mapping relationships may include a mapping relationship between a focus position of the X-ray tube and a ratio of a first boundary intensity to a second boundary intensity described in connection with 1010 and 1020. The mapping table may also record information of detection units corresponding to the first boundary intensity and the second boundary intensity, respectively. Given detection units corresponding to the first boundary intensity and the second boundary intensity, and a ratio of the first boundary intensity to the second boundary intensity, the focus position determination module 720 may determine a focus position corresponding to the ratio by consulting the mapping table. If data in the mapping table is insufficient, the focus position may be obtained using conventional techniques, such as interpolation, extrapolation, etc.

The mapping table may be determined in advance. In some embodiments, the focus position tracker 104 may generate the mapping table automatically. In some embodiments, a user (e.g., a doctor, an imaging engineer, a manufacture of a CT scanner, etc.) may input the mapping table into the focus position tracker 104. In some embodiments, the mapping table may be stored in a storage device (e.g., the storage 106). The focus position determination module 720 may obtain the mapping table by accessing the storage device.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A calibration system for tracking a focus position of an imaging device, wherein the imaging device includes an X-ray tube that has focus positions where X-rays are emitted and an X-ray detector, wherein the calibration system comprises:
   a storage device, configured to store a computer program; and
   a processor, configured to communicate with the storage device, by executing the computer program, causing the system to:
      obtain a first detector response, from the X-ray detector, corresponding to a first focus position by scanning a reference object with the imaging device;
      obtain a second detector response, from the X-ray detector, corresponding to a second focus position by scanning a target object with the imaging device;
      determine, by consulting a correction table, a third detector response corresponding to the first focus position and a fourth detector response corresponding to the second focus position, wherein the correction table includes a correspondence relationship between focus positions and detector responses;
calibrate the first detector response based on the third detector response and the fourth detector response;
obtain image data corresponding to the target object based on the calibrated first detector response and the second detector response; and
generate an image based on the image data.

2. The system of claim 1, wherein the reference object includes air or a phantom, and the target subject includes a patient.

3. The system of claim 1, wherein the correction table is generated by obtaining and recording a plurality of detector responses and corresponding focus positions when a second reference object is scanned.

4. The system of claim 2, the processor further causes the system to:
determine at least one of the first focus position or the second focus position based on a ray intensity distribution detected by an edge detection unit of the X-ray detector of the imaging device, wherein
the imaging device further includes a collimator.

5. The system of claim 3, wherein, to calibrate the first detector response based on the third detector response and the fourth detector response, the processor causes the system to:
determine, based on the third detector response and the fourth detector response, a calibration value; and
calibrate the first detector response based on the calibration value.

6. The system of claim 5, wherein the calibration value is a difference value between the fourth detector response and the third detector response, and wherein the calibrating the first detector response based on the calibration value includes:
adding the difference value to the first detector response.

7. The system of claim 5, wherein the calibration value is a ratio of the fourth detector response to the third detector response, and wherein the calibrating the first detector response based on the calibration value includes:
multiplying the ratio by the first detector response.

8. The system of claim 4, wherein the collimator includes:
an opening, and
a protrusion, the protrusion being configured at at least one end of the opening and protruding into the opening, the opening having a plurality of opening widths along a first direction and a plurality of opening lengths along a second direction, the plurality of opening widths including a first opening width and a second opening width, the first opening width corresponding to at least one end of the collimator in the second direction, the second opening width corresponding to a middle section of the collimator in the second direction, and the first opening width being smaller than the second opening width,
wherein the edge detection unit is located at an edge of the X-ray detector along the first direction, a size of the edge detection unit along the second direction corresponds to a size of a protrusion along the second direction, and each ray intensity of the ray intensity distribution corresponds to a focus position of an X-ray tube.

9. A method for calibrating a focus position of an imaging device, wherein the imaging device includes an X-ray tube that has focus positions where X-rays are emitted and an X-ray detector, wherein the method comprises:
obtaining a first detector response, from the X-ray detector, corresponding to a first focus position by scanning a reference object using the imaging device;
obtaining a second detector response, from the X-ray detector, corresponding to a second focus position by scanning a target object using the imaging device;
determining, by consulting a correction table, a third detector response corresponding to the first focus position and a fourth detector response corresponding to the second focus position, wherein the correction table includes a correspondence relationship between focus positions and detector responses;
calibrating the first detector response based on the third detector response and the fourth detector response;
obtaining image data corresponding to the target object based on the calibrated first detector response and the second detector response; and
generating an image based on the image data.

10. The method of claim 9, wherein the calibrating the first detector response based on the third detector response and the fourth detector response comprises:
determining, based on the third detector response and the fourth detector response, a calibration value; and
calibrating the first detector response based on the calibration value.

11. The method of claim 9, further comprising:
determining the first focus position and/or the second focus position based on a ray intensity distribution detected by an edge detection unit of the X-ray detector of the imaging device, wherein the imaging device further includes a collimator, the collimator includes:
an opening, and
a protrusion, the protrusion being configured at at least one end of the opening and protruding into the opening, the opening having a plurality of opening widths along a first direction and a plurality of opening lengths along a second direction, the plurality of opening widths including a first opening width and a second opening width, the first opening width corresponding to at least one end of the collimator in the second direction, the second opening width corresponding to a middle section of the collimator in the second direction, and the first opening width being smaller than the second opening width,
wherein the edge detection unit is located at an edge of the X-ray detector along the first direction, a size of the edge detection unit along the second direction corresponds to a size of a protrusion along the second direction, and each ray intensity of the ray intensity distribution corresponds to a focus position of an X-ray tube.

12. The method of claim 9, wherein the reference object includes air or a phantom, and the target subject includes a patient.

13. The method of claim 9, further comprising:
generating the correction table by obtaining and recording a plurality of detector responses and corresponding focus positions when scanning a second reference object.

14. The method of claim 10, wherein the calibration value is a difference value between the fourth detector response and the third detector response, and calibrating the first detector response based on the calibration value includes:
adding the difference value to the first detector response.

15. The method of claim 10, wherein the calibration value is a ratio of the fourth detector response to the third detector response, and calibrating the first detector response based on the calibration value includes:
multiplying the ratio by the first detector response.

16. A non-transitory readable medium, comprising at least one set of instructions, wherein when executed by at least one processor of a computing device, the at least one set of instructions directs the at least one processor to perform a method, the method comprising:
obtaining a first detector response corresponding to a first focus position by scanning a reference object;
obtaining a second detector response corresponding to a second focus position by scanning a target object;
determining, by consulting a correction table, a third detector response corresponding to the first focus position and a fourth detector response corresponding to the second focus position, wherein the correction table includes a correspondence relationship between focus positions and detector responses;
calibrating the first detector response based on the third detector response and the fourth detector response;
obtaining image data corresponding to the target object based on the calibrated first detector response and the second detector response; and
generating an image based on the image data.

17. The non-transitory readable medium of claim 16, wherein the reference object includes air or a phantom, and the target subject includes a patient.

18. The non-transitory readable medium of claim 16, the method further comprising:
generating the correction table by obtaining and recording a plurality of detector responses and corresponding focus positions when scanning a second reference object.

19. The non-transitory readable medium of claim 16, wherein calibrating the first detector response based on the third detector response and the fourth detector response includes:
determining, based on the third detector response and the fourth detector response, a calibration value; and
calibrating the first detector response based on the calibration value.

20. The non-transitory readable medium of claim 19, wherein the calibration value is a difference value between the fourth detector response and the third detector response, and calibrating the first detector response based on the calibration value includes:
adding the difference value to the first detector response.

* * * * *